US010874684B2

(12) United States Patent
Davis

(10) Patent No.: US 10,874,684 B2
(45) Date of Patent: Dec. 29, 2020

(54) LIPONUCLEOTIDE-BASED THERAPY FOR ARDS

(71) Applicant: Ohio State Innovation Foundation, Columbus, OH (US)

(72) Inventor: Ian Christopher Davis, Hilliard, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 16/230,225

(22) Filed: Dec. 21, 2018

(65) Prior Publication Data

US 2019/0134074 A1 May 9, 2019

Related U.S. Application Data

(63) Continuation-in-part of application No. PCT/US2017/039545, filed on Jun. 27, 2017.

(60) Provisional application No. 62/355,096, filed on Jun. 27, 2016.

(51) Int. Cl.

| | | |
|---|---|---|
| *A61K 31/7068* | (2006.01) | |
| *A61P 11/00* | (2006.01) | |
| *C07H 19/20* | (2006.01) | |
| *A61K 47/50* | (2017.01) | |

(52) U.S. Cl.
CPC .......... *A61K 31/7068* (2013.01); *A61K 47/50* (2017.08); *A61P 11/00* (2018.01); *C07H 19/20* (2013.01)

(58) Field of Classification Search
None
See application file for complete search history.

(56) References Cited

U.S. PATENT DOCUMENTS

| | | | | |
|---|---|---|---|---|
| 4,386,078 | A * | 5/1983 | Horrocks ............... | A61K 31/70 514/49 |
| 6,258,795 | B1 | 7/2001 | Von Borstel et al. | |
| 2003/0087845 | A1* | 5/2003 | Nyce ...................... | A61K 31/00 514/44 R |
| 2003/0139350 | A1 | 7/2003 | Larsen et al. | |
| 2003/0181353 | A1* | 9/2003 | Nyce ..................... | A61K 31/519 514/1 |
| 2004/0063674 | A1 | 4/2004 | Levy et al. | |
| 2020/0129624 | A1* | 4/2020 | Davis ................... | A61K 47/544 |

OTHER PUBLICATIONS

Short et al., "Pathogenesis of infl uenza-induced acute respiratory distress syndrome" The Lancet vol. 14 pp. 57-69 (Year: 2014).*
Mutlu GM and Sznajder JI. Mechanisms of pulmonary edema clearance. Am J Physiol Lung Cell Mol Physiol 289: L685-L695, 2005.
Zhang Q, Tamura Y, Roy M, Adachi Y, Iijima M and Sesaki H. Biosynthesis and roles of phospholipids in mitochondrial fusion, division and mitophagy. Cell Mol Life Sci 71: 3767-3778, 2014.
Fagone P and Jackowski S. Phosphatidylcholine and the CDP☐ocholine cycle. Biochim Biophys Acta 1831: 523-532, 2013.
Vance JE. Phospholipid synthesis and transport in mammalian cells. Traffic 16: 1-18, 2015.
Kamil B, Anna F, Anna S, Sïawomir P and Halina C. Regulation of sphingomyelin metabolism. Pharmacol Rep 68: 570-581, 2016.
Franks TJ, Colby TV, Travis WD, Tuder RM, Reynolds HY, Brody AR, Cardoso WV, Crystal RG, Drake CJ, Engelhardt J, Frid M, Herzog E, Mason R, Phan SH, Randell SH, Rose MC, Stevens T, Serge J, Sunday ME, Voynow JA, Weinstein BM, Whitsett J and Williams MC. Resident cellular components of the human lung. Proc AM Thorac Soc 5: 763-766, 2008.
Hessel L. Pandemic influenza vaccines: meeting the supply, distribution and deployment challenges. Influenza Other Respir Viruses 3: 165-170, 2009.
Nicoll A, Brown C, Karcher F, Penttinen P, Hegermann-Lindencrone M, Villanueva S, Ciotti M, Jean-Gilles L, Rehmet S and Nguyen-Van-Tam JS. Developing pandemic preparedness in Europe in the 21st century: experience, evolution and next steps. Bull World Health Org 90: 311-317, 2012.
Grohskopf LA, Olsen SJ, Sokolow LZ, Bresee JS, Cox NJ, Broder KR, Karron RA and Walter EB. Prevention and control of seasonal influenza with vaccines: Recommendations of the Advisory Committee on Immunization Practices (ACIP)—United States, 2014-2015 influenza season. MMWR 63: 691-697, 2014.
2015 Two flu vaccine manufacturers announce delays in product delivery. http://www.aafp.org/news/health-ofthe-public/20151021fluvaccdelays.html, 2015.
Whitley RJ and Monto AS. Seasonal and pandemic influenza preparedness: a global threat. J Infect Dis 194 Suppl 2: S65-S69, 2006.
Rolfes M, Blanton L, Brammer L, Smith S, Mustaquim D, Steffens C, Cohen J, Leon M, Chaves SS, Abd Elai Al, Gubareva L, Hall H, Wallis T, Villanueva J, Bresee J, Cox N and Finelli L. Update: Influenza activity—United States, Sep. 28-Dec. 6, 2014. MMWR 63: 1189-1194, 2014.
Short KR, Kroeze EJBV, Fouchier RAM and Kuiken T. Pathogenesis of influenza-induced acute respiratory distress syndrome. Lancet Infect Dis 14: 57-69, 2014.
Matute-Bello G, Downey G, Moore BB, Groshong SD, Matthay MA, Slutsky AS, Kuebler WM and on behalf of the Acute Lung Injury in Animals Study Group. An official American Thoracic Society Workshop Report: Features and measurements of experimental acute lung injury in animals. Am J Respir Cell Mol Biol 44: 725-738, 2011.
Bowman AS, Nelson SW, Edwards JL, Hofer CC, Notting JM, Davis IC and Slemons RD. Comparative effectiveness of isolation techniques for contemporary influenza A virus strains circulating in exhibition swine. J Vet Diagnostic Invest 25: 82-90, 2013.
Hickman-Davis JM, Nicholas-Bevensee C, Davis IC, Ma HP, Davis GC, Bosworth CA and Matalon S. Reactive species mediate inhibition of alveolar type II sodium transport during mycoplasma infection. Am J Respir Crit Care Med 173: 334-344, 2006.

(Continued)

*Primary Examiner* — Eric Olson
(74) *Attorney, Agent, or Firm* — Thomas|Horstemeyer LLP

(57) ABSTRACT

Compositions and method are therefore disclosed for treating ARDS. In particular, disclosed a composition that contains one, two, or more cytidine diphosphate (CDP)-conjugated precursors selected from the group consisting of CDP-choline, CDP-ethanolamine, and CDP-diacylglycerol (CDP-DAG) in a pharmaceutically acceptable carrier for use in treating ARDS.

36 Claims, 11 Drawing Sheets

(56) References Cited

OTHER PUBLICATIONS

Wu Y, Ma J, Woods PS, Chesarino NM, Liu C, Lee LJ, Nana-Sinkam SP and Davis IC. Selective targeting of alveolar type II respiratory epithelial cells by anti-surfactant protein-C antibody-conjugated lipoplexes. J Control Release 203: 140-149, 2015.

Trans-Omics for Precision Medicine (TOPMed) Program. https://www.nhlbi.nih.gov/research/resources/nhlbiprecision-medicine-initiative/topmed, 2016.

Rogers AJ and Matthay MA. Applying metabolomics to uncover novel biology in ARDS. Am J Physiol Lung Cell Mol Physiol 306: L957-L961, 2014.

Hallman M, Spragg R, Harrell JH, Moser KM and Gluck L. Evidence of lung surfactant abnormality in respiratory failure. Study of bronchoalveolar lavage phospholipids, surface activity, phospholipase activity, and plasma myoinositol. J Clin Invest 70: 673-683, 1982.

Günther A, Siebert C, Schmidt R, Ziegler S, Grimminger F, Yabut M, Temmesfeld B, Walmrath D, Morr H and Seeger W. Surfactant alterations in severe pneumonia, acute respiratory distress syndrome, and cardiogenic lung edema. Am J Respir Cult Care Med 153: 176-184, 1996.

Dushianthan A, Goss V. Cusack R, Grocott M and Postle A. Altered molecular specificity of surfactant phosphatidycholine synthesis in patients with acute respiratory distress syndrome. Respir Res 15: 128, 2014.

Schmidt R, Meier U, Yabut-Perez M, Walmrath D, Grimminger F, Seeger W and Günther A. Alteration of fatty acid profiles in different pulmonary surfactant phospholipids in acute respiratory distress syndrome and severe pneumonia. Am J Respir Crit Care Med 163: 95-100, 2001.

Evans CR, Kamovsky A, Kovach MA, Standiford TJ, Burant CF and Stringer KA. Untargeted LC☐MS metabolomics of bronchoalveolar lavage fluid differentiates acute respiratory distress syndrome from health. JProteome Res 13: 640-649, 2014.

Thangavel RR and Bouvier NM. Animal models for influenza virus pathogenesis, transmission, and immunology. J Immunol Methods 410: 60-79, 2014.

Aeffner F, Abdulrahman B, Hickman-Davis JM, Janssen PM, Amer A, Bedwell DM, Sorscher EJ and Davis IC. Heterozygosity for the F508del mutation in the cystic fibrosis transmembrane conductance regulator anion channel attenuates influenza severity. J Infect Dis 208: 780-789, 2013.

Aeffner F, Woods PS and Davis IC. Activation of A1-adenosine receptors promotes leukocyte recruitment to the lung and attenuates acute lung injury in mice infected with influenza A/WSN/33 (H1N1) virus. J Virol 88: 10214-10227, 2014.

Kuiken T, van den Brand J, van Riel D, Pantin-Jackwood M and Swayne DE. Comparative pathology of select agent influenza A virus infections. Vet Path 47: 893-914, 2010.

Otte A and Gabriel G. 2009 pandemic H1N1 influenza A virus strains display differential pathogenicity in C57BL/6J but not BALB/c mice. Virulence 2: 563-566, 2011.

Dushianthan A, Cusack R, Goss V, Postle A and Grocott M. Clinical review: Exogenous surfactant therapy for acute lung injury/acute respiratory distress syndrome—where do we go from here? Crit Care 16: 238, 2012.

Willson DF, Truwit JD, Conaway MR, Traul CS and Egan EE. The adult calfactant in acute respiratory distress syndrome trial. Chest 148: 356-364, 2015.

Tili E, Michaille JJ, Luo Z, Volinia S, Rassenti LZ, Kipps TJ and Croce CM. The down-regulation of miR-125b in chronic lymphocytic leukemias leads to metabolic adaptation of cells to a transformed state. Blood 120: 2631-2638, 2012.

Woods PS, Doolittle LM, Rosas LE, Joseph LM, Calomeni EP and Davis IC. Lethal H1N1 influenza A virus infection alters the murine alveolar type II cell surfactant lipidome. Am J Physiol Lung Cell Mol Physiol, 2016.

Goligher EC, Kavanagh BP, Rubenfeld GD, Adhikari NKJ, Pinto R, Fan E, Brochard LJ, Granton JT, Mercat A, Marie Richard JC, Chretien JM, Jones GL, Cook DJ, Stewart TE, Slutsky AS, Meade MO and Ferguson ND. Oxygenation response to positive end-expiratory pressure predicts mortality in acute respiratory distress syndrome. A secondary analysis of the LOVS and ExPress trials. Am J Respir Crit Care Med 190: 70-76, 2014.

Festic E, Bansal V, Kor DJ, Gajic O and US Critical Illness and Injury Trials Group: Lung Injury Prevention Study Investigators (USCIITG☐LIPS). SpO2/FiO2 ratio on hospital admission is an indicator of early acute respiratory distress syndrome development among patients at risk. J Intensive Care Med 30: 209-216, 2015.

Cotroneo AM, Castagna A, Putignano S, Lacava R, Fanto F, Monteleone F, Rocca F, Malara A and Gareri P. Effectiveness and safety of citicoline in mild vascular cognitive impairment: the IDEALE study. Clin Interv Aging 8: 131-137, 2013.

Parrish WR, Rosas-Ballina M, Gallowitsch-Puerta M, Ochani M, Ochani K, Yang LH, Hudson L, Lin X, Patel N, Johnson SM, Chavan S, Goldstein RS, Czura CJ, Miller EJ, Al-Abed Y, Tracey KJ and Pavlov VA. Modulation of TNF release by choline requires ☐7 subunit nicotinic acetylcholine receptor-mediated signaling. Mol Med 14: 567-574, 2008.

Topuz BB, Altinbas B, Yilmaz MS, Saha S, Batten TF, Savci V and Yalcin M. The effect of centrally injected CDPcholine on respiratory system; involvement of phospholipase to thromboxane signaling pathway. Respir Physiol Neurobiol 195: 50-58, 2014.

Cetinkaya M, Cansev M, Kafa IM, Tayman C, Cekmez F, Canpolat FE, Tunc T and Sarici SU. Cytidine 5'-diphosphocholine ameliorates hyperoxic lung injury in a neonatal rat model. Pediatr Res 74: 26-33, 2013.

Schmidt R, Markart P, Ruppert C, Wygrecka M, Kuchenbuch T, Walmrath D, Seeger W and Guenther A. Timedependent changes in pulmonary surfactant function and composition in acute respiratory distress syndrome due to pneumonia or aspiration. Respir Res 8: 55, 2007.

Matsumoto T, Takahashi H, Shiva D, Kawanishi N, Kremenik MJ, Kato Y and Yano H. The reduction of voluntary physical activity after poly I:C injection is independent of the effect of poly I:C-induced interferon-beta in mice. Physiol Behav 93: 835-841, 2008.

Moreau M, André C, O'Connor JC, Dumich SA, Woods JA, Kelley KW, Dantzer R, Lestage J and Castanon N. Inoculation of Bacillus Calmette-Guerin to mice induces an acute episode of sickness behavior followed by chronic depressive-like behavior. Brain Behav Immun 22: 1087-1095, 2008.

The ARDS Definition Task Force. Acute respiratory distress syndrome: The Berlin definition. JAMA 307: 2526-2533, 2012.

Chen J, Chen Z, Chintagari NR, Bhaskaran M, Jin N, Narasaraju T and Liu L. Alveolar type I cells protect rat lung epithelium from oxidative injury. J Physiol 572: 625-638, 2006.

Durbin JE, Hackenmiller R, Simon MC and Levy DE. Targeted disruption of the mouse Stat1 gene results in compromised innate immunity to viral disease. Cell 84: 443-450, 1996.

Matute-Bello G, Frevert CW and Martin TR. Animal models of acute lung injury. Am J Physiol Lung Cell Mol Physiol 295: L379-L399, 2008.

Cartner SC, Simecka JW, Lindsey JR, Cassell GH and Davis JK. Chronic respiratory mycoplasmosis in C3H/HeN and C57BL/6N mice: lesion severity and antibody response. Infect Immun 63: 4138-4142, 1995.

Haddad IY, Nieves-Cruz B and Matalon S. Inhibition of surfactant function by copper-zinc superoxide dismutase (CuZn-SOD). J Appl Physiol (1985) 83: 1545-1550, 1997.

Matalon S, DeMarco V, Haddad IY, Myles C, Skimming JW, Schurch S, Cheng S and Cassin S. Inhaled nitric oxide injures the pulmonary surfactant system of lambs in vivo. Am J Physiol 270: L273-L280, 1996.

Haddad IY, Holm BA, Hlavaty L and Matalon S. Dependence of surfactant function on extracellular pH: mechanisms and modifications. J Appl Physiol (1985) 76: 657-662, 1994.

International Search Report issued for PCT/US2017/039545, dated Sep. 15, 2017.

Monto AS. Epidemiology of influenza. Vaccine 26 Suppl 4: D45-D48, 2008.

(56) References Cited

OTHER PUBLICATIONS

Kash JC and Taubenberger JK. The role of viral, host, and secondary bacterial factors in influenza pathogenesis. Am J Pathol 185: 1528-1536, 2015.
Johnson NP and Mueller J. Updating the accounts: global mortality of the 1918-1920 "Spanish" influenza pandemic. Bull Hist Med 76: 105-115, 2002.
Monto AS. The threat of an avian influenza pandemic. N Engl J Med 352: 323-325, 2005.
Neumann G, Noda T and Kawaoka Y. Emergence and pandemic potential of swine-origin H1N1 influenza virus. Nature 459: 931-939, 2009.
Li G, Yilmaz M, Kojicic M, Fernández-Pérez E, Wahab R, Huskins WC, Afessa B, Truwit JD and Gajic O. Outcome of critically ill patients with influenza virus infection. J Clin Virol 46: 275-278, 2009.
Aeffner F, Bratasz A, Flaño E, Powell KA and Davis IC. Post-infection A77-1726 treatment improves cardiopulmonary function in H1N1 influenza-infected mice. Am J Respir Cell Mol Biol 47: 543-551, 2012.
Mason RJ. Biology of alveolar type II cells. Respirology 11 Suppl: S12-S15, 2006.
Thompson CI, Barclay WS, Zambon MC and Pickles RJ. Infection of human airway epithelium by human and avian strains of influenza A virus. J Virol 80: 8060-8068, 2006.
Ibricevic A, Pekosz A, Walter MJ, Newby C, Battaile JT, Brown EG, Holtzman MJ and Brody SL. Influenza virus receptor specificity and cell tropism in mouse and human airway epithelial cells. J Virol 80: 7469-7480, 2006.
Wolk KE, Lazarowski ER, Traylor ZP, Yu EN, Jewell NA, Durbin RK, Durbin JE and Davis IC. Influenza A virus inhibits alveolar fluid clearance in BALB/c mice. Am J Respir Crit Care Med 178: 969-976, 2008.
Aeffner F, Traylor ZP, Yu ENZ and Davis IC. Double-stranded RNA induces similar pulmonary dysfunction to respiratory syncytial virus in BALB/c mice. Am J Physiol Lung Cell Mol Physiol 301: L99-L109, 2011.
Traylor ZP, Aeffner F and Davis IC. Influenza A H1N1 induces declines in alveolar gas exchange in mice consistent with rapid post-infection progression from acute lung injury to ARDS. Influenza Other Respir Viruses 7: 472-479, 2013.
Hofer CC, Woods PS and Davis IC. Infection of mice with influenza A/WSN/33 (H1N1) virus alters alveolar type II cell phenotype. Am J Physiol Lung Cell Mol Physiol 308: L628-L638, 2015.
Loosli CG, Stinson SF, Ryan DP, Hertweck MS, Hardy JD and Serebrin R. The destruction of type 2 pneumocytes by airborne influenza PR8-A virus; its effect on surfactant and lecithin content of the pneumonic lesions of mice. Chest 67: 7S-14S, 1975.
Stinson SF, Ryan DP, Hertweck S, Hardy JD, Hwang-Kow SY and Loosli CG. Epithelial and surfactant changes in influenzal pulmonary lesions. Arch Pathol Lab Med 100: 147-153, 1976.
Tam V, Quehenberger O, Oshansky C, Suen R, Armando A, Treuting P, Thomas P, Dennis E and Aderem A. Lipidomic profiling of influenza infection identifies mediators that induce and resolve inflammation. Cell 154: 213-227, 2013.
Morita M, Kuba K, Ichikawa A, Nakayama M, Katahira J, Iwamoto R, Watanebe T, Sakabe S, Daidoji T, Nakamura S, Kadowaki A, Ohto T, Nakanishi H, Taguchi R, Nakaya T, Murakami M, Yoneda Y, Arai H, Kawaoka Y, Penninger J, Arita M and Imai Y. The lipid mediator protectin D1 inhibits influenza virus replication and improves severe influenza. Cell 153: 112-125, 2013.
Milner JJ, Rebeles J, Dhungana S, Stewart DA, Sumner SCJ, Meyers MH, Mancuso P and Beck MA. Obesity increases mortality and modulates the lung metabolome during pandemic H1N1 influenza virus infection in mice. J Immunol 194: 4846-4859, 2015.
Agassandian M and Mallampalli RK. Surfactant phospholipid metabolism. Biochim Biophys Acta 1831: 612-625, 2013.
Goss V, Hunt AN and Postle AD. Regulation of lung surfactant phospholipid synthesis and metabolism. Biochim Biophys Acta 1831: 448-458, 2013.

Reichert TA, Simonsen L, Sharma A, Pardo SA, Fedson DS and Miller MA. Influenza and the winter increase in mortality in the United States, 1959-1999. Am J Epidemiol 160: 492-502, 2004.
Thompson WW, Shay DK, Weintraub E, Brammer L, Cox N, Anderson LJ and Fukuda K. Mortality associated with influenza and respiratory syncytial virus in the United States. JAMA 289: 179-186, 2003.
Peiris JS, de Jong MD and Guan Y. Avian influenza virus (H5N1): a threat to human health. Clin Microbiol Rev 20: 243-267, 2007.
Taubenberger JK and Morens DM. Influenza: the once and future pandemic. Public Health Rep 125 Suppl 3: 16-26, 2010.
Shoham D. Influenza type A virus: an outstandingly protean pathogen and a potent modular weapon. Crit Rev Microbiol 39: 123-138, 2012.
Robertson JS and Inglis SC. Prospects for controlling future pandemics of influenza. Virus Res 162: 39-46, 2011.
Kieny MP and Fukuda K. The pandemic influenza vaccine challenge. Vaccine 26, Suppl 4: D3-D4, 2008.
Osterholm MT, Kelley NS, Sommer A and Belongia EA. Efficacy and effectiveness of influenza vaccines: a systematic review and meta-analysis. Lancet Infect Dis 12: 36-44, 2012.
Kaiser L, Wat C, Mills T, Mahoney P, Ward P and Hayden F. Impact of oseltamivir treatment on influenzarelated lower respiratory tract complications and hospitalizations. Arch Intern Med 163: 1667-1672, 2003.
Cochrane Neuraminidase Inhibitors Review Team. Does oseltamivir really reduce complications of influenza? Clin Infect Dis 53: 1302-1303, 2011.
Dunn AG, Arachi D, Hudgins J, Tsafnat G, Coiera E and Bourgeois FT. Financial conflicts of interest and conclusions about neuraminidase inhibitors for influenza: An analysis of systematic reviews. Ann Intern Med 161: 513-518, 2014.
Westall G and Paraskeva M. H1N1 influenza: Critical care aspects. Semin Respir Crit Care Med 32: 400-408, 2011.
Wang CY, Calfee CS, Paul DW, Janz DR, May AK, Zhuo H, Bernard GR, Matthay MA, Ware LB and Kangelaris KN. One-year mortality and predictors of death among hospital survivors of acute respiratory distress syndrome. Intensive Care Med 40: 388-396, 2014.
Ruthman CA and Festic E. Emerging therapies for the prevention of acute respiratory distress syndrome. Ther Adv Respir Dis 9: 173-187, 2015.
Martinello RA. Preparing for avian influenza. Curr Opin Pediatr 19: 64-70, 2007.
Herzog EL, Brody AR, Colby TV, Mason R and Williams MC. Knowns and unknowns of the alveolus. Proc Am Thorac Soc 5: 778-782, 2008.
Dobbs LG, Johnson MD, Vanderbilt J, Allen L and Gonzalez R. The great big alveolar TI cell: Evolving concepts and paradigms. Cell Physiol Biochem 25: 55-62, 2010.
Corti M, Brody AR and Harrison JH. Isolation and primary culture of murine alveolar type II cells. Am J Respir Cell Mol Biol 14: 309-315, 1996.
Davis IC and Matalon S. Epithelial sodium channels in the adult lung—important modulators of pulmonary health and disease. Adv Exp Med Biol 618: 127-140, 2007.
Marconett CN, Zhou B, Rieger ME, Selamat SA, Dubourd M, Fang X, Lynch SK, Stueve TR, Siegmund KD, Berman BP, Borok Z and Laird-Offringa IA. Integrated transcriptomic and epigenomic analysis of primary human lung epithelial cell differentiation. PLoS Genet 9: e1003513, 2013.
Whitsett JA, Wert SE and Weaver TE. Alveolar surfactant homeostasis and the pathogenesis of pulmonary disease. Ann Rev Med 61: 105-119, 2010.
Bernardino de la Serna J, Hansen S, Berzina Z, Simonsen AC, Hannibal-Bach HK, Knudsen J, Ejsing CS and Bagatolli LA. Compositional and structural characterization of monolayers and bilayers composed of native pulmonary surfactant from wild type mice. Biochim Biophys Acta 1828: 2450-2459, 2013.
Vance JE and Tasseva G. Formation and function of phosphatidylserine and phosphatidylethanolamine in mammalian cells. Biochim Biophys Acta 1831: 543-554, 2013.

(56) References Cited

OTHER PUBLICATIONS

Lottes RG, Newton DA, Spyropoulos DD and Baatz JE. Lactate as substrate for mitochondrial respiration in alveolar epithelial type II cells. Am J Physiol Lung Cell Mol Physiol 308: L953-L961, 2015.
Mejia EM and Hatch GM. Mitochondrial phospholipids: role in mitochondrial function. J Bioenerg Biomembr 48: 99-112, 2015.
Horvath SE and Daum G. Lipids of mitochondria. Prog Lipid Res 52: 590-614, 2013.
Ha EEJ and Frohman MA. Regulation of mitochondrial morphology by lipids. BioFactors 40: 419-424, 2014.
Li XX, Tsoi B, Li YF, Kurihara H and He RR. Cardiolipin and its different properties in mitophagy and apoptosis. J Histochem Cytochem 63: 301-311, 2015.
Alli AA, Brewer EM, Montgomery DS, Ghant MS, Eaton DC, Brown LA and Helms MN. Chronic ethanol exposure alters the lung proteome and leads to mitochondrial dysfunction in alveolar type 2 cells. Am J Physiol Lung Cell Mol Physiol 306: L1026-L1035, 2014.
Tate MD, Pickett DL, Van Rooijen N, Brooks AG and Reading PC. Critical role of airway macrophages in modulating disease severity during influenza virus infection of mice. J Virol 84: 7569-7580, 2010.
Tate MD, Deng YM, Jones JE, Anderson GP, Brooks AG and Reading PC. Neutrophils ameliorate lung injury and the development of severe disease during influenza infection. J Immunol 183: 7441-7450, 2009.
Lottes RG, Newton DA, Spyropoulos DD and Baatz JE. Alveolar type II cells maintain bioenergetic homeostasis in hypoxia through metabolic and molecular adaptation. Am J Physiol Lung Cell Mol Physiol 306: L947-L955, 2014.
Nakahira K, Kyung SY, Rogers AJ, Gazourian L, Youn S, Massaro AF, Quintana C, Osorio JC, Wang Z, Zhao Y, Lawler LA, Christie JD, Meyer NJ, Causland FRM, Waikar SS, Waxman AB, Chung RT, Bueno R, Rosas IO, Fredenburgh LE, Baron RM, Christiani DC, Hunninghake GM and Choi AMK. Circulating mitochondrial DNA in patients in the ICU as a marker of mortality: Derivation and validation. PLoS Med 10: e1001577, 2014.
Sun S, Sursal T, Adibnia Y, Zhao C, Zheng Y, Li H, Otterbein LE, Hauser CJ and Itagaki K. Mitochondrial DAMPs increase endothelial permeability through neutrophil dependent and independent pathways. PLoS ONE 8: e59989, 2013.
El-Hattab AW and Scaglia F. Disorders of carnitine biosynthesis and transport. Mol Genet Metab 116: 107-112, 2015.
Guzy RD, Sharma B, Bell E, Chandel NS and Schumacker PT. Loss of the SdhB, but not the SdhA, subunit of complex II triggers reactive oxygen species-dependent hypoxia-inducible factor activation and tumorigenesis. Mol Cell Biol 28: 718-731, 2008.
Vohwinkel CU, Hoegl S and Eltzschig HK. Hypoxia signaling during acute lung injury. J Appl Physiol 119: 1157, 2015.
Rutter J, Winge DR and Schiffman JD. Succinate dehydrogenase □ Assembly, regulation and role in human disease. Mitochondrion 10: 393-401, 2010.
Tseng YC, Kulp SK, Lai IL, Hsu EC, He WA, Frankhouser DE, Yan PS, Mo X, Bloomston M, Lesinski GB, Marcucci G, Guttridge DC, Bekaii-Saab T and Chen CS. Preclinical investigation of the novel histone deacetylase inhibitor AR-42 in the treatment of cancer-induced cachexia. J Natl Cancer Inst 107: 2015.
Jao CY, Roth M, Welti R and Salic A. Metabolic labeling and direct imaging of choline phospholipids in vivo. Proc Natl Acad Sci USA 106: 15332-15337, 2009.
Haspel JA, Chettimada S, Shaik RS, Chu JH, Raby BA, Cernadas M, Carey V, Process V, Hunninghake GM, Ifedigbo E, Lederer JA, Englert J, Pelton A, Coronata A, Fredenburgh LE and Choi AMK. Circadian rhythm reprogramming during lung inflammation. Nat Commun 5: 2014.
Dobbs LG. Isolation and culture of alveolar type II cells. Am J Physiol Lung Cell Mol Physiol 258: L134-L147, 1990.
Iwatsuki H, Sasaki K, Suda M and Itano C. Cell differentiation of alveolar epithelium in the developing rat lung: ultrahistochemical studies of glycoconjugates on the epithelial cell surface. Histochemistry 100: 331-340, 1993.
Chen Z, Jin N, Narasaraju T, Chen J, McFarland LR, Scott M and Liu L. Identification of two novel markers for alveolar epithelial type I and II cells. Biochem Biophys Res Commun 319: 774-780, 2004.
Cocuron JC and Alonso AP. Liquid chromatography tandem mass spectrometry for measuring 13C-labeling in intermediates of the glycolysis and pentose phosphate pathway. Methods Mol Biol 1090: 131-142, 2014.
Koubaa M, Cocuron JC, Thomasset B and Alonso AP. Highlighting the tricarboxylic acid cycle: Liquid and gas chromatography□mass spectrometry analyses of 13C-labeled organic acids. Anal Biochem 436: 151-159, 2013.
Nguyen TN, Padman BS and Lazarou M. Deciphering the molecular signals of PINK1/Parkin mitophagy. Trends Cell Biol 26: 733-744, 2016.
Mao P, Wu S, Li J, Fu W, He W, Liu X, Slutsky AS, Zhang H and Li Y. Human alveolar epithelial type II cells in primary culture. Physiol Rep 3: 2015.
Wu W, Zhang W, Booth JL and Metcalf JP. Influenza A(H1N1)pdm09 virus suppresses RIG-I initiated innate antiviral responses in the human lung. PLoS ONE 7: e49856, 2012.
Ryan AJ, Fisher K, Thomas CP and Mallampalli RK. Transcriptional repression of the CTP:phosphocholine cytidylyltransferase gene by sphingosine. Biochem J 382: 741-750, 2004.
Roy SS, Mukherjee S, Kabir S, Rajaratnam V, Smith M and Das SK. Inhibition of cholinephosphotransferase activity in lung injury induced by 2-chloroethyl ethyl sulfide, a mustard analog. J Biochem Mol Toxicol 19: 289-297, 2005.
Wu Y, Xu Z, Henderson FC, Ryan AJ, Yahr TL and Mallampalli RK. Chronic Pseudomonas aeruginosa infection reduces surfactant levels by inhibiting its biosynthesis. Cell Microbiol 9: 1062-1072, 2007.
Henderson FC, Miakotina OL and Mallampalli RK Proapoptotic effects of P. aeruginosa involve inhibition of surfactant phosphatidylcholine synthesis. J Lipid Res 47: 2314-2324, 2006.
Zhou J, Ryan AJ, Medh J and Mallampalli RK. Oxidized lipoproteins inhibit surfactant phosphatidylcholine synthesis via calpain-mediated cleavage of CTP:phosphocholine cytidylyltransferase. J Biol Chem 278: 37032-37040, 2003.
Mallampalli RK, Ryan AJ, Salome RG and Jackowski S. Tumor necrosis factor-α inhibits expression of CTP:phosphocholine cytidylyltransferase. J Biol Chem 275: 9699-9708, 2000.
Cornell RB and Ridgway ND. CTP:phosphocholine cytidylyltransferase: Function, regulation, and structure of an amphitropic enzyme required for membrane biogenesis. Prog Lipid Res 59: 147-171, 2015.
Ridsdale R, Tseu I, Wang J and Post M. CTP:phosphocholine cytidylyltransferase □ is a cytosolic protein in pulmonary epithelial cells and tissues. J Biol Chem 276: 49148-49155, 2001.
Agassandian M, Zhou J, Tephly LA, Ryan AJ, Carter AB and Mallampalli RK. Oxysterols inhibit phosphatidylcholine synthesis via ERK docking and phosphorylation of CTP:phosphocholine cytidylyltransferase. J Biol Chem 280: 21577-21587, 2005.
Ryan AJ, Andrews M, Zhou J and Mallampalli RK. c-Jun N-terminal kinase regulates CTP:phosphocholine cytidylyltransferase. Arch Biochem Biophys 447: 23-33, 2006.
Planz O. Development of cellular signaling pathway inhibitors as new antivirals against influenza. Antiviral Res 98: 457-468, 2013.
Jain R, Barkauskas CE, Takeda N, Bowie EJ, Aghajanian H, Wang Q, Padmanabhan A, Manderfield LJ, Gupta M, Li D, Li L, Trivedi CM, Hogan BLM and Epstein JA. Plasticity of Hopx+ type I alveolar cells to regenerate type II cells in the lung. Nat Commun 6: 6727, 2015.
Barkauskas CE, Cronce MJ, Rackley CR, Bowie EJ, Keene DR, Stripp BR, Randell SH, Noble PW and Hogan BLM. Type 2 alveolar cells are stem cells in adult lung. J Clin Invest 123: 3025-3036, 2013.

(56) References Cited

OTHER PUBLICATIONS

Morton CC, Aitchison AJ, Gehrig K and Ridgway ND. A mechanism for suppression of the CDP-choline pathway during apoptosis. J Lipid Res 54: 3373-3384, 2013.

van Kuilenburg AB, Meinsma R, Vreken P, Waterham HR and van Gennip AH. Isoforms of human CTP synthetase. Adv Exp Med Biol 486: 257-261, 2000.

* cited by examiner

MOCK DAY 6　　　　WSN DAY 6　　　　WSN DAY 6 – CDP-CHOLINE-Tx

LIPONUCLEOTIDE-BASED THERAPY FOR ARDS

CROSS-REFERENCE TO RELATED APPLICATIONS

This application is a continuation-in-part of copending International Application Serial No. PCT/US2017/038545, filed Jun. 27, 2017, which claims benefit of U.S. Provisional Application No. 62/355,096, filed Jun. 27, 2016, which are hereby incorporated herein by reference in their entirety.

STATEMENT REGARDING FEDERALLY SPONSORED RESEARCH OR DEVELOPMENT

This invention was made with Government Support under Grant No. HL102469 awarded by the National Institutes of Health. The Government has certain rights in the invention.

BACKGROUND

Acute respiratory distress syndrome (ARDS, also known as acute lung injury or acute hypoxemic respiratory failure) is a clinical syndrome characterized by acute onset of severely impaired alveolar gas exchange. ARDS can be caused by both direct lung insults (infection, toxic gas inhalation, etc.) or as an indirect result of trauma, sepsis, or other bodily insults. Approximately 200,000 human ARDS cases occur per year in the US. ARDS can also develop in other animals. Once ARDS has developed, the only treatment option is nonspecific supportive management in the ICU. Currently, approximately 40% of human patients with any form of ARDS die and many more are left with severe deficits in lung function and reduced quality of life.

Influenza is the 8th leading cause of attributable annual human mortality in the USA, accounting for approximately 200,000 hospitalizations and greater than 30,000 excess deaths per year. Influenza also has significant pandemic potential. For example, the 1918 "Spanish flu" pandemic resulted in more than 50 million deaths worldwide. Influenza also has potential as a biological warfare and bioterrorism agent. Approximately 20% of patients with severe influenza develop ARDS, which is associated with poor prognosis. There is a great need for new treatments that can prevent, retard, or manage progression of severe influenza to ARDS: this is also true for ARDS from other causes.

Pulmonary surfactant, which is primarily composed of phospholipids, is essential to normal lung function and is synthesized by alveolar type II (ATII) cells. Phospholipids are also vital to many other aspects of cellular and organellar metabolism and function. Phospholipid content of bronchoalveolar lavage fluid (BALF) from ARDS patients is often low, although the mechanisms underlying this effect have not been defined. Direct administration of artificial surfactant (e.g., Survanta) into the lungs is highly effective in treating neonatal respiratory distress syndrome (neonatal RDS) in humans. However, recent trials of surfactant replacement therapy in human ARDS patients were inconclusive or showed no benefit.

SUMMARY

Development of influenza-induced ARDS is shown herein to result from reduced levels of cytidine diphosphate (CDP)-conjugated liponucleotide precursors for phospholipid synthesis in ATII cells. This is accompanied by reduced BALF surfactant phospholipid content. The disclosed data indicate that influenza infection results in decreased synthesis of CDP-conjugated liponucleotide precursors for phospholipid synthesis by ATII cells. This may occur directly as a result of influenza viral infection of and/or replication in said cell, or indirectly as a result of the effect of host factors currently known or to be discovered in the future that are induced in other cells in response to viral infection acting on said cell. Therefore, as disclosed herein, supplementation with the liponucleotides CDP-choline, CDP-ethanolamine, CDP-diacylglycerol (CDP-DAG), or any combination thereof, either prior to or after onset of injury or disease has occurred can bypass the block(s) in phospholipid synthesis resulting from reduced liponucleotide synthesis and thereby improve ATII cell phospholipid synthesis in a cell being susceptible to an injury which causes normal phospholipid production of said cell to become retarded and/or completely inhibited. This supplementation can result in increased ATII cell and surfactant phospholipid levels, thereby promoting improved ATII cell and lung function. This will prevent or retard development of ARDS in influenza-infected subjects, or will reduce severity of ongoing ARDS and will thereby increase influenza survival rates and reduce incidence and severity of long-term clinical sequelae associated with ARDS and mechanical ventilation. These include, but are not limited to, reduced lung function, pulmonary fibrosis, depression, post-traumatic stress disorder, and others known to those skilled in the art. In contrast, supplementation with the CDP-choline precursors CTP and choline, either separately or in combination has no such effect. Because similar decreases in BALF surfactant levels have been described for ARDS caused by other insults, this therapy could have general patient outcome benefits in various delivery modalities and the wide applicability for ARDS.

An additional reason for the focus on these lipids is that they are vital to many other aspects of cellular and organellar metabolism and function. ATII cells have high metabolic activity and are therefore heavily dependent on mitochondrial (Mi) function for energy production. Mi function is also important for other lung cells. Mi membranes contain large amounts of phospholipids, which play an important role in maintaining normal Mi structure and function. Hence, alterations in phospholipid synthesis may also impair Mi viability, function and generation of ATP. This will have consequences for ATII cell function. A change in Mi phospholipid composition could also promote mitophagy, Mi-dependent ATII cell apoptosis, and release of Mi DNA, which can have pro-inflammatory effects and may contribute to development of ARDS. The data disclosed herein show that development of influenza-induced ARDS is associated with dysregulated oxidative phosphorylation and abnormal mitochondrial (Mi) morphology in ATII cells, which can be reversed by treatment with CDP-choline. Therefore, as disclosed herein, supplementation with the liponucleotides CDP-choline, CDP-ethanolamine, CDP-DAG, or any combination thereof, can bypass the block(s) in phospholipid synthesis resulting from reduced liponucleotide synthesis and thereby improve Mi structure and function in an ATII cell and/or other lung cells being susceptible to an injury which causes normal phospholipid production of said cell to become retarded, impaired, and/or completely inhibited.

The plasma membranes and lipid membranes of all other cellular organelles in all lung cells known or to be discovered in the future will all be expected to contain large amounts of phospholipids, which are essential to the normal function of said organelles. Hence, alterations in phospholipid synthesis will impair plasma membrane and organelle membrane integrity and function. This will have consequences for ATII cell and other lung cell function and viability. Therefore, supplementation with the liponucleotides CDP-choline, and/or CDP-ethanolamine, and/or CDP-DAG, with or without chemical modifications, can bypass the block in phospholipid synthesis resulting from reduced liponucleotide synthesis and thereby improve ATII cell and other lung cell plasma membrane and organelle structure and function in a cell being susceptible to an injury which causes normal phospholipid production of said cell to become retarded and or completely inhibited.

Compositions and methods are therefore disclosed for preventing, retarding development of, or treating ARDS. For example, a composition is disclosed that contains one, two, or more cytidine diphosphate (CDP)-conjugated precursors selected from the group consisting of CDP-choline, CDP-ethanolamine, and CDP-DAG in a pharmaceutically acceptable carrier.

DAG is a glyceride consisting of two fatty acid (acyl) chains covalently bonded to a glycerol molecule through ester linkages. Two possible forms exist, 1,2-diacylglycerols and 1,3-diacylglycerols. In some embodiments, the CDP-DAG contains acyl chains derived from short-chain fatty acids (with aliphatic tails containing fewer than 6 carbons), medium-chain fatty acids (with aliphatic tails containing 6-12 carbons), long-chain fatty acids (with aliphatic tails containing 13-21 carbons), or very long-chain fatty acids (with aliphatic tails containing more than 22 carbons). Fatty acids may be of natural origin or generated by chemical synthesis, according to any methods known to those skilled in the art. In some embodiments, the two acyl chains are in the 1,2 positions. In some embodiments, the two acyl chains are in the 1,3 positions. In some embodiments, both acyl chains are of the same length (contain the same number of carbons). In some embodiments, the two acyl chains are of different lengths. In some embodiments, one or both acyl chains of the DAG component of CDP-DAG are mono-unsaturated (containing one double bond in cis and/or trans configuration). In some embodiments, one or both acyl chains of the DAG component of CDP-DAG are poly-unsaturated (containing more than one double bond in cis and/or trans configuration). In some embodiments, one or both acyl chains of the DAG component of CDP-DAG are saturated (containing no double bonds). In some embodiments, one or both acyl chains are chemically modified. Chemical modifications include, but are not limited to, methylation, esterification, amidation, nitration, nitrosylation, oxidation, sulfation, acetylation, alcoholysis, acidolysis, biotinylation, conjugation to fluorophores, and other modifications known to those skilled in the art.

In some embodiments, the CDP component of CDP-choline is chemically modified. Chemical modifications include, but are not limited to, methylation, esterification, amidation, nitration, nitrosylation, oxidation, sulfation, acetylation, alcoholysis, acidolysis, biotinylation, conjugation to fluorophores, and other modifications known to those skilled in the art.

In some embodiments, the CDP component of CDP-ethanolamine is chemically modified. Chemical modifications include, but are not limited to, methylation, esterification, amidation, nitration, nitrosylation, oxidation, sulfation, acetylation, alcoholysis, acidolysis, biotinylation, conjugation to fluorophores, and other modifications known to those skilled in the art.

In some embodiments, the CDP component of CDP-DAG is chemically modified. Chemical modifications include, but are not limited to, methylation, esterification, amidation, nitration, nitrosylation, oxidation, sulfation, acetylation, alcoholysis, acidolysis, biotinylation, conjugation to fluorophores, and other modifications known to those skilled in the art.

In some embodiments, the choline component of CDP-choline is chemically modified. Chemical modifications include, but are not limited to, methylation, esterification, amidation, nitration, nitrosylation, oxidation, sulfation, acetylation, alcoholysis, acidolysis, biotinylation, conjugation to fluorophores, and other modifications known to those skilled in the art.

In some embodiments, the ethanolamine component of CDP-ethanolamine is chemically modified. Chemical modifications include, but are not limited to, methylation, esterification, amidation, nitration, nitrosylation, oxidation, sulfation, acetylation, alcoholysis, acidolysis, biotinylation, conjugation to fluorophores, and other modifications known to those skilled in the art.

In some embodiments, the glycerol component of CDP-DAG is chemically modified. Chemical modifications include, but are not limited to, methylation, esterification, amidation, nitration, nitrosylation, oxidation, sulfation, acetylation, alcoholysis, acidolysis, biotinylation, conjugation to fluorophores, and other modifications known to those skilled in the art.

In some embodiments, a mixture of two or more CDP-choline precursors with or without different chemical modifications of CDP and/or choline can be incorporated.

In some embodiments, a mixture of two or more CDP-ethanolamine precursors with or without different chemical modifications of CDP and/or ethanolamine chains can be incorporated.

In some embodiments, a mixture of two or more CDP-DAG precursors with or without different acylations or chemical modifications of CDP and/or acyl chains can be incorporated.

In some embodiments, the CDP-conjugated precursors are collectively present at a unit dose of at least 0.1 ng/kg, including 0.1, 0.2, 0.3, 0.4, 0.5, 0.6, 0.7, 0.8, 0.9, 1.0 ng/kg.

In some embodiments, the CDP-choline and/or CDP-ethanolamine and/or CDP-DAG are present in equal concentrations or ratios. In some embodiments, at least two of the CDP-conjugated precursors are present in equal concentrations or ratios, which can be higher or lower than the third CDP-conjugated precursor, which may be absent. In some cases, one of the CDP-conjugated precursors is present at a concentration or ratio that is at least 2, 3, 4, 5, 6, 7, 8, 9, or 10 fold higher than one or both of the other CDP-conjugated precursors.

The disclosed compositions can further contain other active and inactive ingredients. For example, in some embodiments, the composition can contain additional lipid moieties, nucleotides, organic acids, amino acids, or sugars.

Also disclosed is a method for preventing development of ARDS in a subject that involves administering to the subject an effective amount of a composition comprising a CDP-conjugated precursor selected from the group consisting of CDP-choline, CDP-ethanolamine, CDP-DAG, and combinations thereof as prophylaxis prior to infection with one or more influenza virus strains.

Also disclosed is a method for preventing development of ARDS in a subject that involves administering to the subject an effective amount of a composition comprising a CDP-conjugated precursor selected from the group consisting of CDP-choline, CDP-ethanolamine, CDP-DAG, and combinations thereof after the subject has been infected with one or more influenza virus strains but before said subject has developed ARDS.

Also disclosed is a method for treating ARDS in a subject that involves administering to the subject with ARDS an effective amount of a composition comprising a CDP-conjugated precursor selected from the group consisting of CDP-choline, CDP-ethanolamine, CDP-DAG, and combinations thereof.

The disclosed methods can be used to prevent, retard development of, or treat any form of ARDS, which can be caused by both direct lung insults (e.g. infection, toxic gas inhalation, cancer, acid aspiration, chest trauma, etc.) or as an indirect result of trauma to other body regions, sepsis, ischemia/reperfusion, surgery, or other causes (see Table 1). In some cases, the ARDS is caused by influenza or by other respiratory viral, bacterial, or fungal infections.

In some cases, the lung insult is a nonn-gas but injurious materials, which can be either biologic or non-biologic. In some cases, the lung insult is vomit, protein (includes enzymes), gastric contents, or ingested food/liquids that are aspirated. In some cases, the lung insult is a gas, liquid, or particulate. Examples of gas insults include metals, chlorine, bromine, tear gas. Examples of liquid insults include paint and paint components, solvents (inorganic and organic acid), acids, bases. Examples of solid insults include particulates from combustion, fine particulates (fly ash, etc.), asbestos, dry powder coatings, and environmental contaminants. Radioactive materials can cause also cause ARDS.

In some cases, the subject has a $PaO_2/FiO_2$ ratio of about 550-750 mmHg 100 kPa) which would be considered normal clinically. Alternatively, the subject has an arterial $O_2$ saturation of greater than 92%. In other cases, the subject has normal lung compliance and no evidence of non-cardiogenic pulmonary edema by radiography, CT scan, magnetic resonance imaging, or other imaging modalities present and future. In some cases, sound medical judgment may dictate that the subject requires prophylactic treatment as a result of having co-morbidities associated with increased risk of influenza infection and/or development of ARDS including, but not limited to, type I diabetes mellitus, type II diabetes mellitus, obesity, pregnancy, epilepsy, pre-existing pulmonary disease, pre-existing cardiovascular disease, pre-existing renal disease, or any other co-morbidity currently known to be or identified in the future as being associated with increased risk of developing ARDS. In other cases, the subject may be clinically normal but require prophylactic treatment as a result of increased risk of exposure to influenza viruses, influenza-infected subjects, or other known causes of ARDS, in order to preserve availability of essential personnel.

In some cases, the subject has a $PaO_2/FiO_2$ ratio of about 201-300 mmHg ($\leq$39.9 kPa), 101-200 mmHg ($\leq$26.6 kPa), or 100 mmHg ($\leq$13.3 kPa). In some cases, the subject has a $PaO_2/FiO_2$ ratio of less than 300 mmHg, less than 200 mmHg, or less than 100 mmHg. These 3 categories correspond to mild, moderate and severe ARDS, as currently defined clinically by the Berlin criteria. In other cases, the subject may have a $PaO_2/FiO_2$ ratio of about 300-550 mmHg ($\leq$73.3 kPa), which would be considered moderately abnormal clinically. Alternatively, the subject has an arterial $O_2$ saturation of less than 92%. In other cases, the subject has a reduced lung compliance or evidence of non-cardiogenic pulmonary edema by radiography, CT scan, magnetic resonance imaging, or other imaging modalities present and future. The subject may exhibit alterations in other measures that may have been or will be found to be associated with ARDS presence and severity in either clinical or experimental situations, including, but not limited to, impaired alveolar fluid clearance, elevated pro-inflammatory cytokines, chemokines, and other inflammatory mediators in lung and/or blood, decreased anti-inflammatory cytokines, chemokines, and other inflammatory mediators in lung and/or blood, increased leukocytes in lung and/or blood, and increased cell death in lung tissue.

The disclosed composition can be administered, for example, intravenously, orally, intramuscular, intraperitoneally, by intrapulmonary instillation, or by inhalation (e.g., aerosolized dry powder or nebulized droplet). Compositions delivered by different routes may contain different formulations.

In some embodiments, the method further involves treating the subject with surfactant therapy. In some embodiments, the method further involves treating the subject with tracheal intubation, tracheotomy, tracheostomy, mechanical ventilation, with or without positive end-expiratory pressure (PEEP), prone or supine positioning, supplemental oxygen, nitric oxide, extracorporeal membrane oxygenation, beta-adrenergic agonists or antagonists, corticosteroids and other anti-inflammatory agents, antibiotics, antiviral drugs, antifungal drugs, cytokines, stem cells from any source, intravenous fluids, whole blood or blood components, parenteral or enteral nutritional formulations, vasodilators, vasoconstrictors, diuretics, insulin or other synthetic or natural hormones, or any combination thereof, or any other treatments found to be beneficial in future experimental and/or clinical situations.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
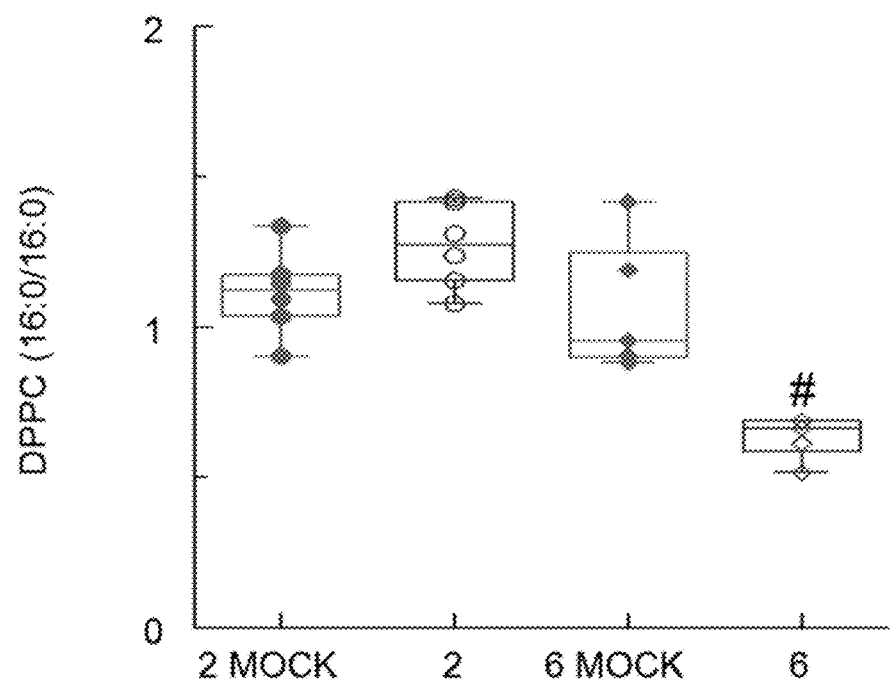
FIG. 1 is a plot showing effect of infection on ATII cell DPPC (16:0/16:0) surfactant. #=P<0.001.

The term "subject" refers to any individual who is the target of administration or treatment. The subject can be a vertebrate, for example, a mammal or bird. Thus, the subject can be a human or veterinary patient. The term "patient" refers to a subject under the treatment of a clinician, e.g., physician or veterinarian, as well as other allied health professionals, including nurses, physician's assistants, and pharmacists.

The term "therapeutically effective" refers to the amount of the composition used is of sufficient quantity to ameliorate one or more causes, symptoms, and/or clinical signs of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms and/or clinical signs rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The disclosed methods can be used to prevent or treat any form of ARDS, which can be caused by both direct lung insults (infection, toxic gas inhalation, cancer, acid aspiration, chest trauma, etc.) or as an indirect result of trauma to other body regions, sepsis, ischemia/reperfusion, or surgery. In some cases, the ARDS is caused by influenza or by other respiratory viral, bacterial, or fungal infections.

In some embodiments, the disclosed methods can be used to treat cardiogenic pulmonary edema, pulmonary trauma and/or hemorrhage, pulmonary ischemia, or pulmonary embolism. Additional primary ARDS indications and non-ARDS uses are described in Table 1.

TABLE 1

| Indication | Cause of ARDS* | Cause of non-ARDS lung injury or dysfunction |
|---|---|---|
| Pneumonia/pneumonitis associated with infectious diseases (bacterial, viral, fungal) | YES | YES |
| Sepsis, septicemia, SIRS (infectious and non-infectious) | YES | YES |
| Exposure to toxic vapors (natural and synthetic), irritant gases, products of combustion, chemical warfare agents, or pollutants by inhalation or any other any route | YES | YES |
| Aspiration of gastric contents, acids, alkalis, or other irritants | YES | YES |
| Pancreatitis | YES | YES |
| Near drowning resulting in aspiration of fresh or salt water into lungs | YES | YES |
| Burns | YES | YES |
| Chest or other trauma | YES | YES |
| Diffuse alveolar or other pulmonary hemorrhage | YES | YES |
| Extrapulmonary hemorrhage and/or hypovolemic shock | YES | YES |
| Lung transplantation | YES | YES |
| Cardiopulmonary bypass | YES | YES |
| Transfusion-related acute lung injury (TRALI) resulting from massive blood transfusion | YES | YES |
| Bone marrow transplantation | YES | YES |
| Pulmonary embolism (fat, air, other), ischemia, atelectasis | YES | YES |
| Mechanical ventilation and ventilator-induced lung injury | YES | YES |
| Hyperoxia | YES | YES |
| Cardiogenic pulmonary edema resulting from acute myocardial infarction, cardiac arrhythmia, or other causes of acute or chronic heart failure | YES | YES |
| Neoplasia (primary and/or metastatic lung cancer and injurious effects of cancers in other organs on lung function) | YES | YES |
| Neonatal respiratory distress syndrome | YES | YES |
| Multi-organ dysfunction syndrome (MODS) | YES | YES |
| Iatrogenic and side-effects of pharmacologics, antineoplastic drugs, radiographic contrast media, nutritional supplements, alternative medicines, and other biologics administered by inhalation or any other route | YES | YES |
| Drug overdose (e.g., aspirin, cocaine, opioids, phenothiazenes, trcicyclics, and the like) | YES | YES |
| Asthma, anaphylactic shock, autoimmunity, allergy, immune suppression, or other intra- and extra-pulmonary conditions resulting from genetic or acquired abnormalities in host immune function | YES | YES |
| Neurogenic pulmonary edema due to stroke, seizure, head trauma, anoxia, and other neurologic injuries or defects | YES | YES |
| Idiopathic acute interstitial pneumonia (Hamman-Rich syndrome) and other idiopathic causes of lung injury | YES | YES |
| Other causes of ARDS known or yet to be discovered | YES | YES |

*According to Berlin definition plus any subsequent modifications to the current clinical definition of ARDS The ARDS-associated cancer of the disclosed methods can be any cell in a subject undergoing unregulated growth, invasion, or metastasis that directly or indirectly results in a form of ARDS. In some cases cancer is a primary or secondary cancer in the lungs. In some case, the cancer is not present in the lung, but the cancer, or treatment of the cancer, causes injury to the lungs.

In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

Cytidine diphosphate-choline (CDP-choline) is a naturally occurring compound that is synthesized from cytidine-5'-triphosphate and phosphocholine with accompanying production of inorganic pyrophosphate in a reversible reaction catalyzed by the enzyme CTP:phosphocholine cytidylyltransferase-α (pcyt1a). CDP-ethanolamine is synthesized from cytidine-5'-triphosphate and phosphoethanolamine with accompanying production of inorganic pyrophosphate in a reversible reaction catalyzed by the enzyme CTP-phosphoethanolamine cytidyltransferase (pcyt2).

The molecular structure of CDP-choline is provided below.

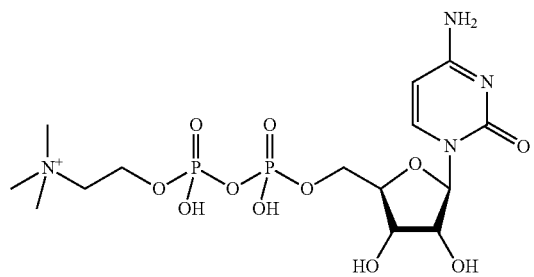

The molecular structure of CDP-ethanolamine is provided below.

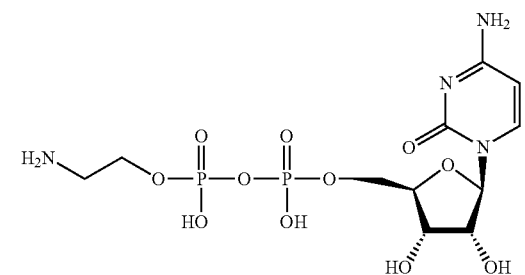

Molecular structures of CDP-DAG are provided below.

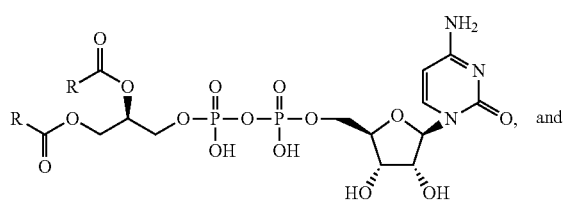

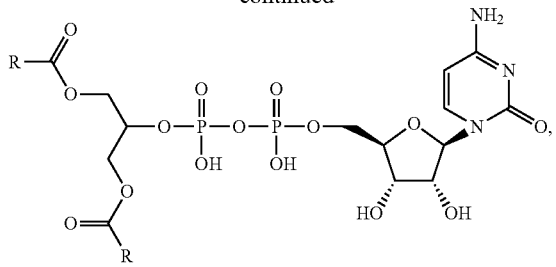

In these structures, R denotes points of attachment of various length acyl chains to the glycerol moiety of CDP-DAG.

The compositions disclosed can be used therapeutically in combination with a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Pharmaceutical carriers are known to those skilled in the art. These most typically would be standard carriers for administration of drugs to humans or animals, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients, such as antimicrobial agents, anti-inflammatory agents, anesthetics, vaccine antigens, adjuvants, and DAMPs.

Preparations for enteral and/or parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Enteral and parenteral vehicles include sodium chloride solution, Ringer's dextrose, dextrose and sodium chloride, lactated Ringer's, glucose, or fixed oils. Intravenous vehicles include fluid and nutrient replenishers, electrolyte replenishers (such as those based on Ringer's dextrose), and the like. Mucosal vehicles include sterile aqueous or non-aqueous solutions, suspensions, and emulsions. Examples include sodium chloride solution, Ringer's dextrose, dextrose and sodium chloride, lactated Ringer's, glucose, fixed oils, propylene glycol, and the like. Preservatives and other additives may also be present such as, for example, antimicrobials, anti-oxidants, chelating agents, and inert gases.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The herein disclosed compositions, including pharmaceutical composition, may be administered in a number of ways depending on whether the desired treatment is prophylactic, for prevention of development of ARDS in influenza-infected and/or other at-risk persons, or for acute treatment of persons with ARDS. For example, the disclosed compositions can be administered orally in powder or tablet form for prophylaxis and prevention of ARDS or given intravenously, intraperitoneally, intramuscularly, subcutaneously, intracavity, or transdermally for treatment of ARDS. Pharmaceutical grade compositions may be administered orally as a compounded tablet including active ingredients at appropriate doses, excipients, and coatings for easing swallowing, and/or controlling release rate of active ingredients, and for shelf life extension. Pharmaceutical grade compositions may be administered orally as a liquid suspension or emulsion. Pharmaceutical grade compositions may be administered parenterally (e.g., intravenously with appropriate carriers, and stabilizers), by intramuscular injection, by intraperitoneal injection, transdermally, extracorporeally, ophthalmically, vaginally, rectally, intranasally, topically or the like, including topical intranasal administration or administration by inhalant.

In one embodiment, the disclosed compositions are administered in a dose equivalent to parenteral administration of about 0.1 ng to about 100 g per kg of body weight, about 10 ng to about 50 g per kg of body weight, about 100 ng to about 1 g per kg of body weight, from about 1 µg to about 100 mg per kg of body weight, from about 1 µg to about 50 mg per kg of body weight, from about 1 mg to about 500 mg per kg of body weight; and from about 1 mg to about 50 mg per kg of body weight. Alternatively, the amount of the disclosed compositions administered to achieve a therapeutic effective dose is about 0.1 ng, 1 ng, 10 ng, 100 ng, 1 µg, 10 µg, 100 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

A number of embodiments of the invention have been described. Nevertheless, it will be understood that various modifications may be made without departing from the spirit and scope of the invention. Accordingly, other embodiments are within the scope of the following claims.

EXAMPLES

Example 1

FIG. 1 is a plot showing effect of infection on ATII cell DPPC (16:0/16:0) surfactant. #=P<0.001.

Figure 2:
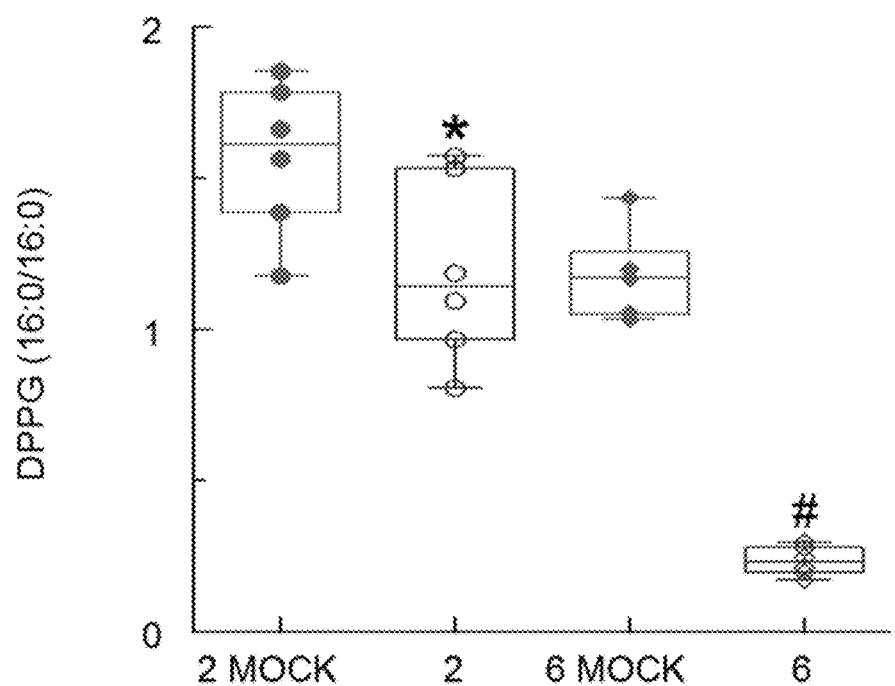
FIG. 2 is a plot showing effect of infection on ATII cell DPPG (16:0/16:0) surfactant. *=P<0.05, #=P<0.001.

FIG. 2 is a plot showing effect of infection on ATII cell DPPG (16:0/16:0) surfactant. *=P<0.05, #=P<0.001.

Figure 3:
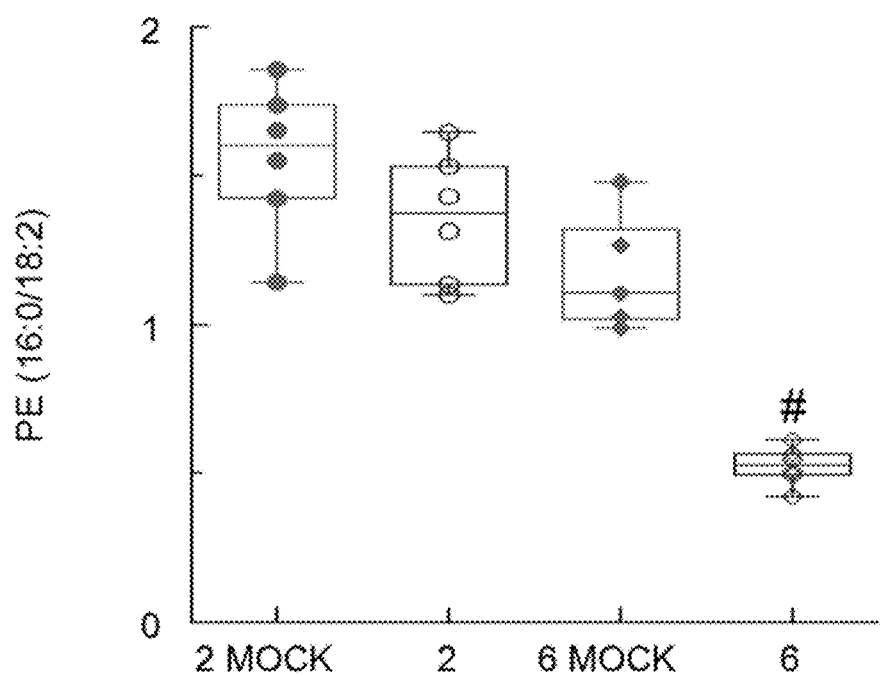
FIG. 3 is a plot showing effect of infection on ATII cell PE (16:0/18:2) surfactant. #=P<0.001.

FIG. 3 is a plot showing effect of infection on ATII cell PE (16:0/18:2) surfactant. #=P<0.001.

Figure 4:
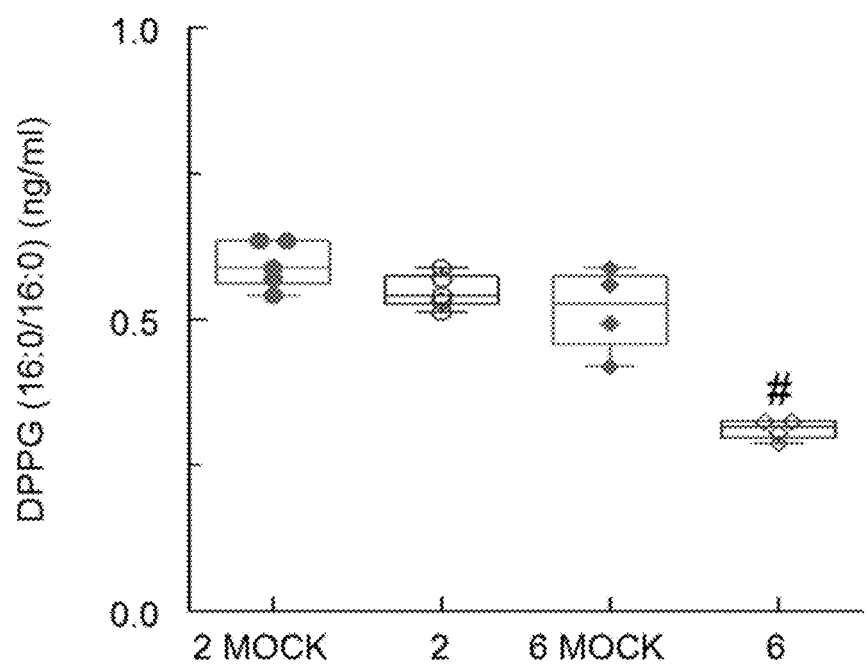
FIG. 4 is a plot showing effect of infection on BALF phospholipid glycerol. #=P<0.001.

FIG. 4 is a plot showing effect of infection on BALF phospholipid glycerol. #=P<0.001.

Figure 5:
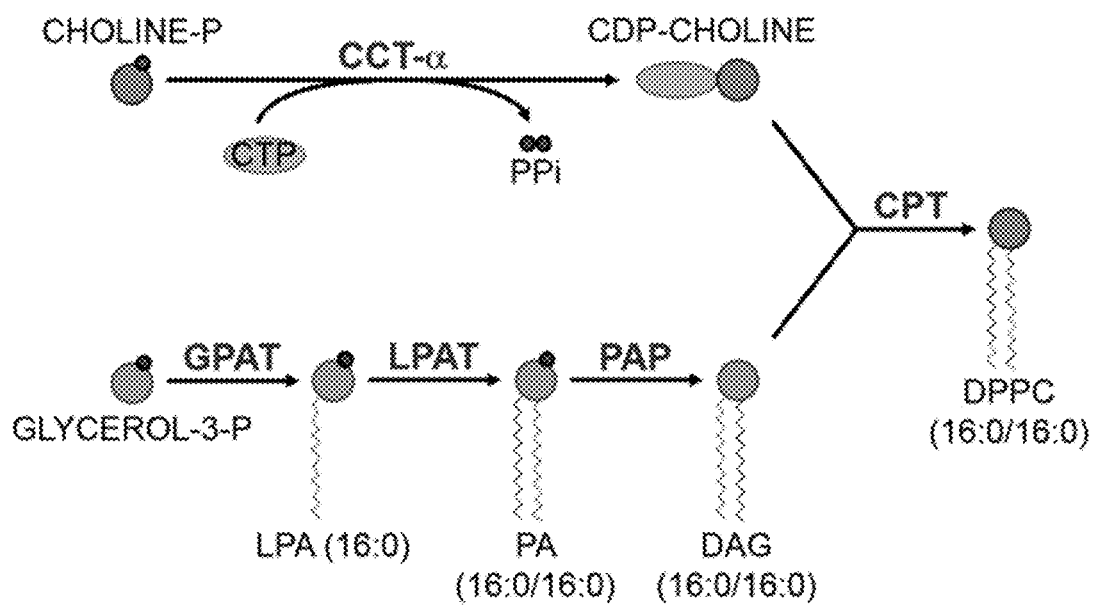
FIG. 5 is a schematic showing DPPC synthesis by the CDP-choline (Kennedy) pathway.

FIG. 5 is a schematic showing DPPC synthesis by the CDP-choline (Kennedy) pathway.

Figure 6:
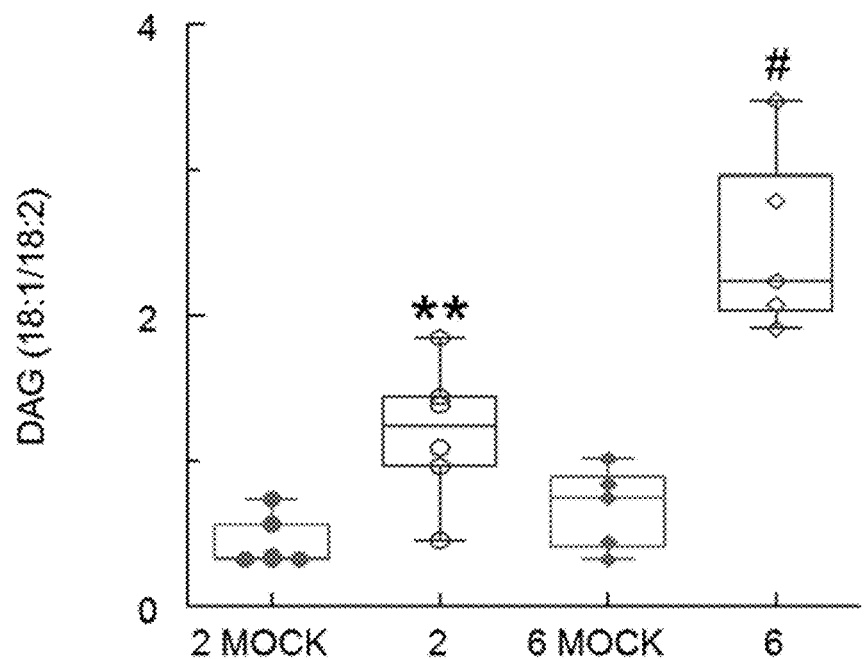
FIG. 6 is a plot showing effect of infection on ATII cell DAG (18:1/18:2). *=P<0.05, #=P<0.001.

FIG. 6 is a plot showing effect of infection on ATII cell DAG (18:1/18:2). *=P<0.05, #=P<0.001.

Figure 7:
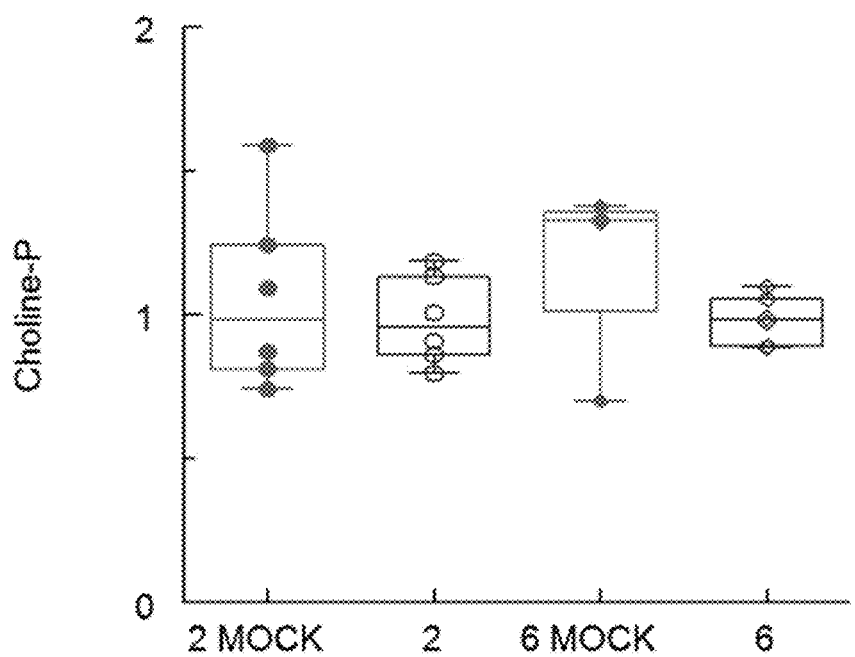
FIG. 7 is a plot showing effect of infection on ATII cell choline-P (18:1/18:2).

FIG. 7 is a plot showing effect of infection on ATII cell choline-P (18:1/18:2).

Figure 8:
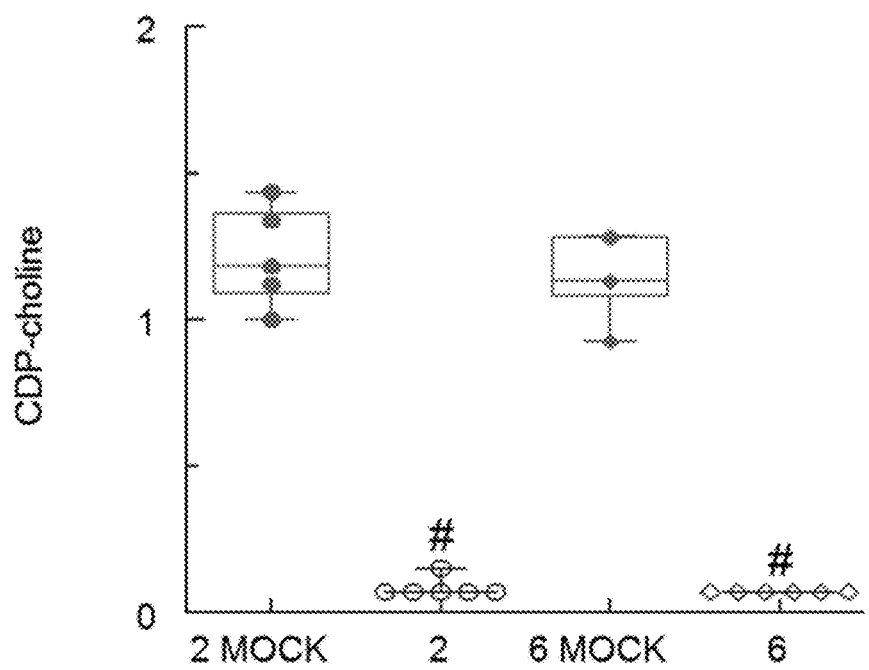
FIG. 8 is a plot showing effect of infection on ATII cell CDP-choline.

FIG. 8 is a plot showing effect of infection on ATII cell CDP-choline.

Figure 9:
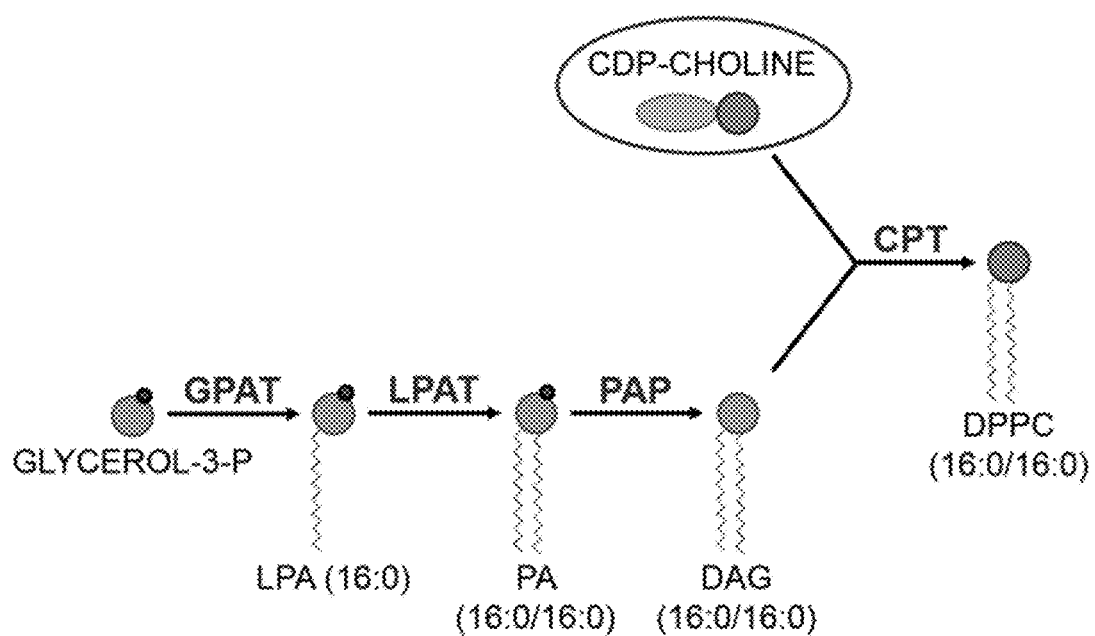
FIG. 9 is a schematic showing therapeutic approach.

FIG. 9 is a schematic showing therapeutic approach.

Figure 10:
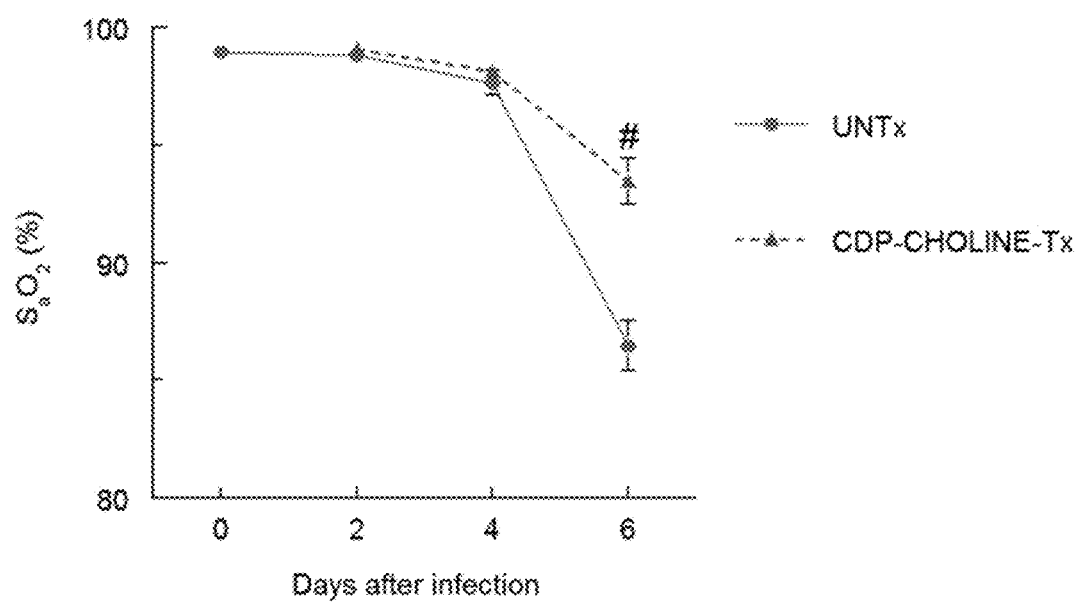
FIG. 10 is a graph showing effect of CDP-choline treatment (▲) on mouse $O_2$ SATS as a function of time (days after infection). #=P<0.001.

FIG. 10 is a graph showing effect of CDP-choline treatment (▲) on mouse $O_2$ SATS as a function of time (days after infection). #=P<0.001.

Figure 11:
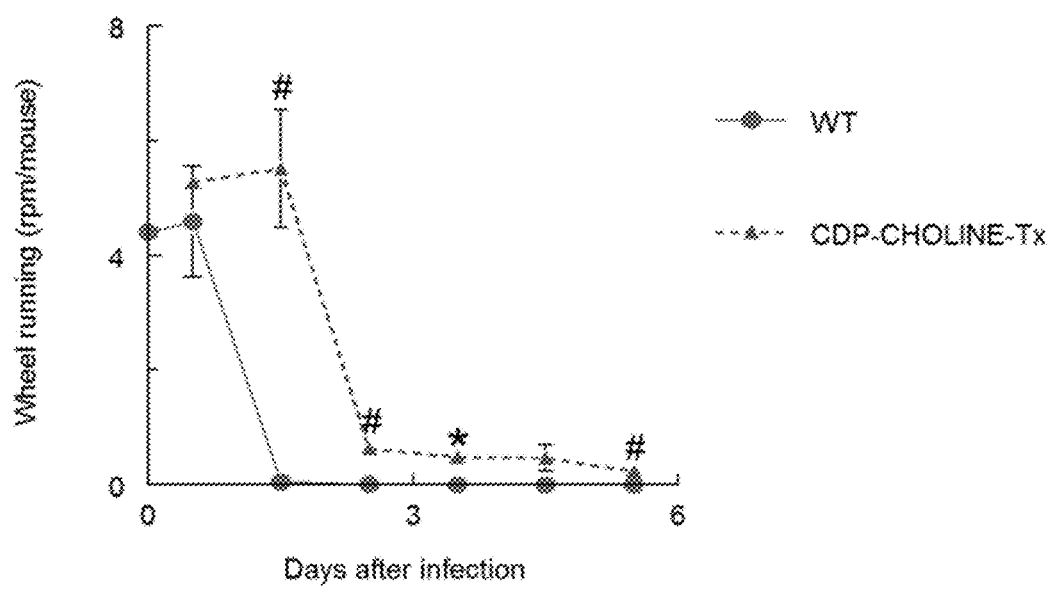
FIG. 11 is a graph showing effect of CDP-choline treatment (▲) on mouse activity (rmp/mouse) as a function of time (days after infection). *=P<0.05, #=P<0.001.

FIG. 11 is a graph showing effect of CDP-choline treatment (▲) on mouse activity (rmp/mouse) as a function of time (days after infection). *=P<0.05, #=P<0.001.

Figure 12:
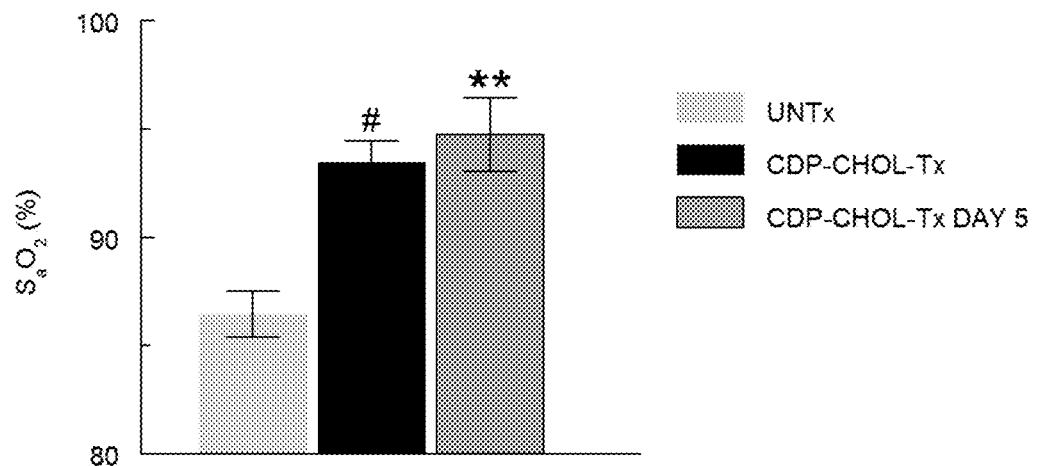
FIG. 12 is a bar graph showing effect of day 5 only CDP-choline treatment on mouse $O_2$ SATS. *=P<0.05, #=P<0.001.
Figure 13:
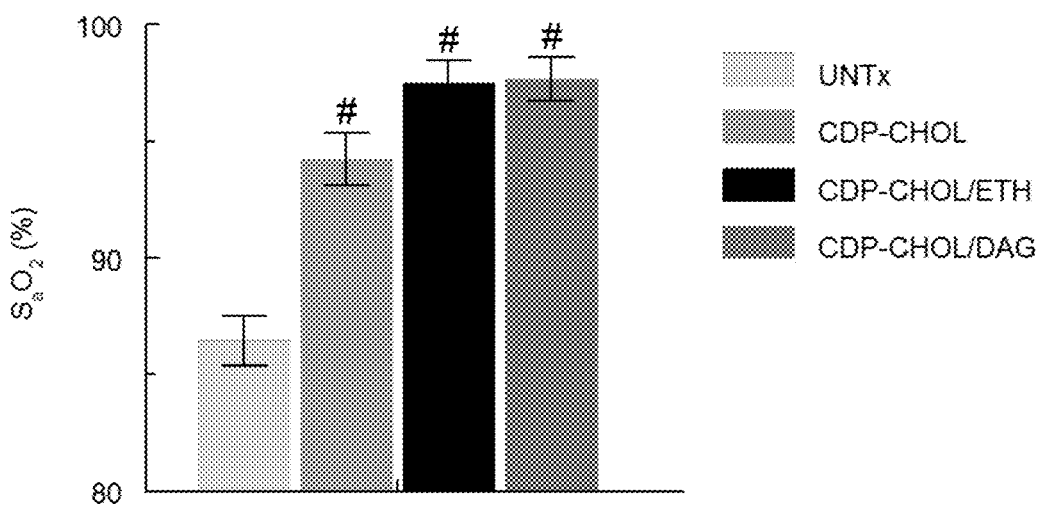
FIG. 13 is a bar graph showing effect of formulation treatment on mouse $O_2$ SATS. #=P<0.001.

FIG. 12 is a bar graph showing effect of day 5 only CDP-choline treatment on mouse $O_2$ SATS. *=P<0.05, #=P<0.001.

CDP-choline improved oxygenation. $S_aO2$ increased from approximately 85% to approximately 96%. This is equivalent to an increase in $P_aO_2$ from approximately 65 mmHg to approximately 85 mmHg. It is also equivalent to an increase in $O_2$ carrying capacity of blood ($C_aO_2$) from approximately 88% to approximately 97% of normal. Patients with an $S_aO_2$ of 96% or a $P_aO_2$ of 96% would not require additional treatment CDP-choline improved cardiac function and resulted in better lung function and reduced pulmonary edema. Effects of single dose treatment late in infection are as good as those of daily treatment throughout course of infection.

lamellae. CDP-choline treatment improves lamellar body morphology. Mi in ATII cells from CDP-choline-treated mice are also more electron-dense and have more normal cristae.

Example 4

Figure 15:
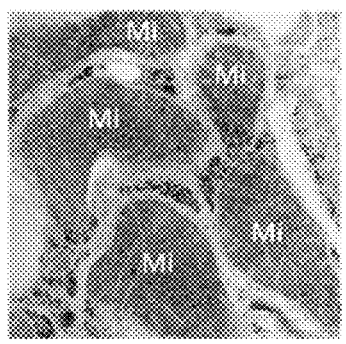
FIG. 15 is a group of 3 transmission electron micrographs showing effects of influenza infection on ultrastructure of ATII cell mitochondria (Mi).
Figure 15:
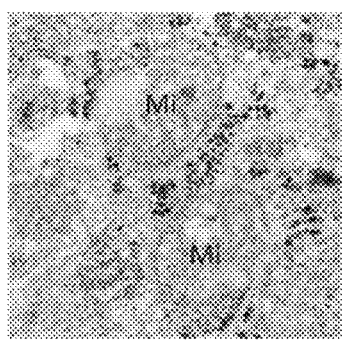
Figure 15:
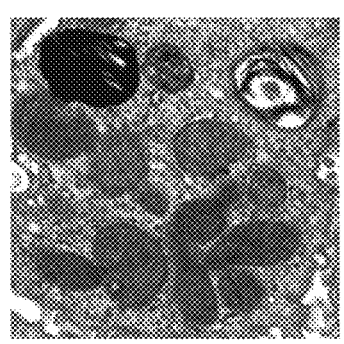

FIG. 15 is a group of 3 transmission electron micrographs showing effects of influenza infection on ultrastructure of ATII cell mitochondria (Mi). Relative to mock-infected controls (left), Mi in ATII cells from A/WSN/33 (H1N1)-infected mice (center) are fewer in number, less electron dense, and have disordered membranes and cristae. Mi in ATII cells from A/WSN/33 (H1N1)-infected mice treated with CDP-choline display normal morphology.

Example 5

Table 3 shows the effect of influenza infection and oral liponulceotide treatment on lung function.

Table 4 shows the effect of influenza infection and CDP-choline treatment on ATII cell ultrastructure.

Table 5 shows the effect of influenza infection and CDP-choline treatment on lung inflammation.

Table 6 shows the effect of influenza infection and CDP-choline treatment on mitochondrial function.

TABLE 2

Effect of influenza infection and i.p. liponucleotide treatment on lung function.

|  | $S_aO_2$ (%) | HR (bpm) | WET:DRY | $R_{BASAL}$ | $C_{ST}$ |
|---|---|---|---|---|---|
| UNINFECTED | 99.0 ± 0.2 | 710 ± 10 | 4.2 ± 0.1 | 0.74 ± 0.03 | 0.1 ± 0.007 |
| DAY 6 MOCK CDP-CHO | 99.0 ± 0.2 | 730 ± 10 | — | 0.99 ± 0.03 | 0.05 ± 0.002 |
| DAY 6 UNTREATED | 86.5 ± 1.1 | 490 ± 10 | 7.1 ± 0.2 | 2.28 ± 0.17 | 0.04 ± 0.002 |
| DAY 6 CDP-CHO | 93.5 ± 1.0# | 570 ± 10* | 6.2 ± 0.4* | 1.96 ± 0.12 | 0.05 ± 0.002# |
| DAY 6 CDP-ETH | 91.1 ± 1.5 | 540 ± 20* | 6.5 ± 0.4 | — | — |
| DAY 6 CDP-DAG | 95.2 ± 1.6* | 600 ± 10** | 5.8 ± 0.1** | — | — |
| DAY 6 CDP-CHO + CDP-ETH | 97.5 ± 0.9# | 620 ± 10* | 6.9 ± 0.2 | — | — |
| DAY 6 CDP-CHO + CDP-DAG | 97.7 ± 0.9# | 600 ± 70 | 5.5 ± 0.2# | 1.54 ± 0.11* | 0.04 ± 0.02 |
| DAY 6 CDP-ETH + CDP-DAG | 78.7 ± 3.3 | 470 ± 40 | 6.7 ± 0.2 | — | — |
| DAY 6 CDP-CHO + CDP-ETH + CDP-DAG | 94.9 ± 1.1* | 620 ± 50* | 6.5 ± 0.9 | — | — |
| DAY 6 CDP-CHO ON DAY 5 ONLY | 92.9 ± 1.5* | 550 ± 10 | 6.2 ± 0.2 | 1.63 ± 0.22* | 0.05 ± 0.006* |

MOCK: Inoculated with virus diluent (0.1% FBS in normal saline)
CDP-CHO: CDP-choline (100 μg/mouse in 50 ☐l saline i.p., daily from 1-5 days post-infection or on day 5 only, as indicated)
CDP-ETH: CDP-ethanolamine (100 μg/mouse)
CDP-DAG: CDP-diacylglycerol (10 μg/mouse)
*P < 0.05,
**P < 0.005,
P < 0.001, vs. DAY 6 UNTREATED

Example 2

Table 2 shows the effect of CDP-conjugated precursor combinations.

Example 3

Figure 14:
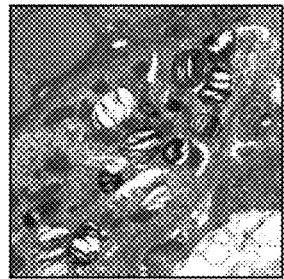
FIG. 14 is a group of three transmission electron micrographs showing effects of CDP-choline treatment on ultrastructure of ATII cell lamellar bodies (composed of surfactant lipids and proteins).
Figure 14:
Figure 14:
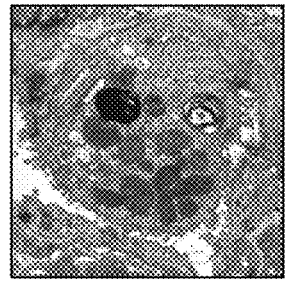

FIG. 14 is a group of three transmission electron micrographs showing effects of CDP-choline treatment on ultrastructure of ATII cell lamellar bodies (composed of surfactant lipids and proteins). Relative to mock-infected controls, lamellar bodies in ATII cells from influenza A/WSN/33 (H1N1)-infected mice are smaller and have disordered

TABLE 3

|  | $S_aO_2$ (%) | HR (bpm) |
|---|---|---|
| UNINFECTED | 99.0 ± 0.2 | 710 ± 10 |
| DAY 6 UNTREATED | 86.5 ± 1.1 | 490 ± 10 |
| DAY 6 SALINE VEHICLE-TREATED | 87.1 ± 2.8 | 460 ± 20 |
| DAY 6 CDP-CHO + CDP-DAG | 91.9 ± 2.6(*) | 570 ± 40* |

CDP-CHO + CDP-DAG: CDP-choline (100 μg/mouse) + CDP-diacylglycerol (10 μg/mouse) by oral gavage, daily from 1-5 days post-infection
(*)P = 0.0516,
*P < 0.05, vs. DAY 6 UNTREATED

TABLE 4

|  | DAY 6 MOCK | DAY 6 UNTREATED | DAY 6 FLU + CDP-CHO |
|---|---|---|---|
| ATII CELL AREA ($\mu m^2$) | 30.37 ± 2.98 | 72.04 ± 3.63 | 53.64 ± 5.63* |
| LAMELLAR BODIES/CELL | 14.27 ± 1.32 | 12.05 ± 0.93 | 8.1 ± 1.16* |
| LAMELLAR BODY AREA ($\mu m^2$) | 0.47 ± 0.06 | 0.59 ± 0.44 | 0.41 ± 0.04* |
| MITOCHONDRIAL/CELL | 16 ± 2.31 | 17.75 ± 2.85 | 14.5 ± 1.78* |
| MITOCHONDRIAL AREA ($\mu m^2$) | 0.43 ± 0.02 | 0.2 ± 0.01 | 0.34 ± 0.01* |

CDP-CHO: CDP-choline (100 μg/mouse in 50 μl saline i.p., daily from 1-5 days post-infection)
*$P < 0.05$, vs. day 6 untreated

TABLE 5

|  | DAY 6 MOCK | DAY 6 UNTREATED | DAY 6 FLU + CDP-CHO |
|---|---|---|---|
| BALF ALVEOLAR MACS ($\times 10^6$/ml) | — | 2.67 ± 0.51 | 1.08 ± 0.21* |
| BALF NEUTROPHILS ($\times 10^6$/ml) | — | 1.69 ± 0.16 | 0.45 ± 0.07** |
| BALF PC | — | 0.79 ± 0.12 | 1.61 ± 0.45* |
| VIRAL TITER (log PFU/g) | 0 | 5.32 ± 0.07 | 5.32 ± 0.07 |

CDP-CHO: CDP-choline (100 μg/mouse in 50 μl saline i.p., daily from 1-5 days post-infection)
*$P < 0.05$,
**$P < 0.005$,
: $P < 0.001$, vs. day 6 untreated

TABLE 6

|  | DAY 6 MOCK | DAY 6 UNTREATED | DAY 6 FLU + CDP-CHO |
|---|---|---|---|
| MITOCHONDRIAL ATP PRODUCTION | 40.54 ± 4.91 | 20.36 ± 1.3 | 36.91 ± 6.82# |
| MITOCHONDRIAL MEMBRANE POTENTIAL ($\psi_m$; DilC$_1$(5) MCF) | 12.29 ± 0.42 | 6.89 ± 0.38 | 10.14 ± 2.3* |

CDP-CHO: CDP-choline (100 μg/mouse in 50 μl saline i.p., daily from 1-5 days post-infection)
*$P < 0.05$,
**$P < 0.005$,
$P < 0.001$, vs. day 6 untreated Example 6

Figure 16:
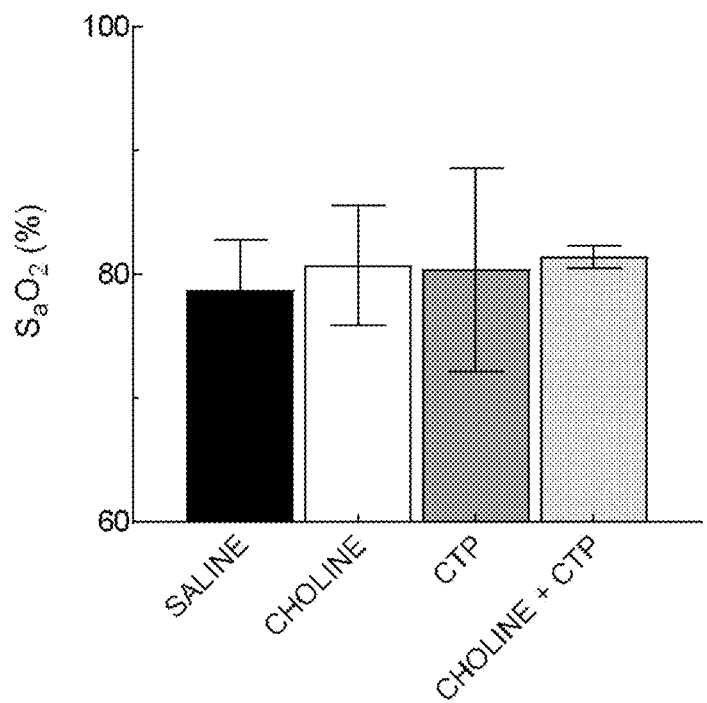
FIG. 16 is a plot showing effect of daily i.p. treatment with choline (100 μg/mouse), cytidine triphosphate (CTP, 100 μg/mouse), and choline+CTP from 1-5 days post-influenza infection on mouse O2 sats (SaO2) at day 6 post-influenza infection. These data demonstrate that the beneficial effects of treatment with the liponucleotide CDP-choline on arterial oxygenation cannot be reproduced by treatment with its precursors (CTP and choline) either given separately or in combination at comparable doses.

The beneficial effects of treatment with the liponucleotide CDP-choline on arterial oxygenation cannot be reproduced by treatment with its precursors (CTP and choline) either given separately or in combination (FIG. 16).

Figure 17:
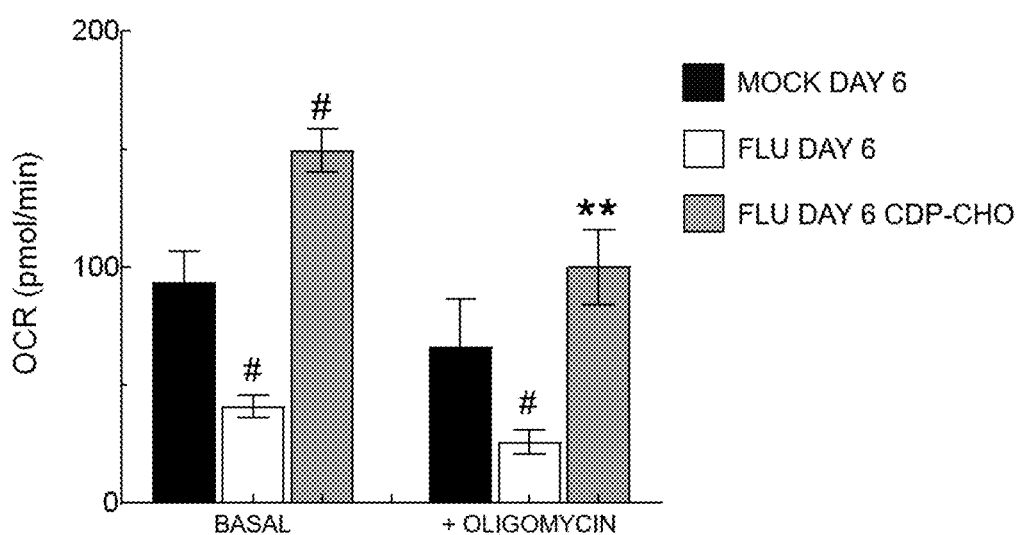
FIG. 17 is a plot showing effect of daily i.p. treatment with CDP-choline (CDP-CHO, 100 μg/mouse) from 1-5 days post-influenza infection on basal O2 consumption rate (OCR) of alveolar type II (ATII) epithelial cells isolated at 6 days post-mock infection or 6 days post-influenza infection and OCR after subsequent treatment of the same ATII cells with oligomycin (1 μM). $**=P<0.005$, $\#=P<0.001$. These data were generated using the Seahorse MitoStress test kit on a Seahorse XFe24 Analyzer (both Agilent, Santa Clara, Calif.) in accordance with manufacturer's instructions. The results demonstrate that influenza infection impairs ATII cell mitochondrial oxidative phosphorylation (basal OCR) and ATP synthase activity (OCR after oligomycin) and demonstrate that these effects are reversed by treatment with CDP-choline.

Influenza infection impairs ATII cell mitochondrial oxidative phosphorylation (basal OCR) and ATP synthase activity (OCR after oligomycin) and demonstrate that these effects are reversed by treatment with CDP-choline (FIG. 17). To generate these data alveolar type II (ATII) epithelial cells were isolated at 6 days post-mock infection or 6 days post-influenza infection and immediately subjected to analysis using the Seahorse MitoStress Kit on a Seahorse XFe24 Analyzer (both Agilent, Santa Clara, Calif.) in accordance with manufacturer's instructions.

Figure 18:
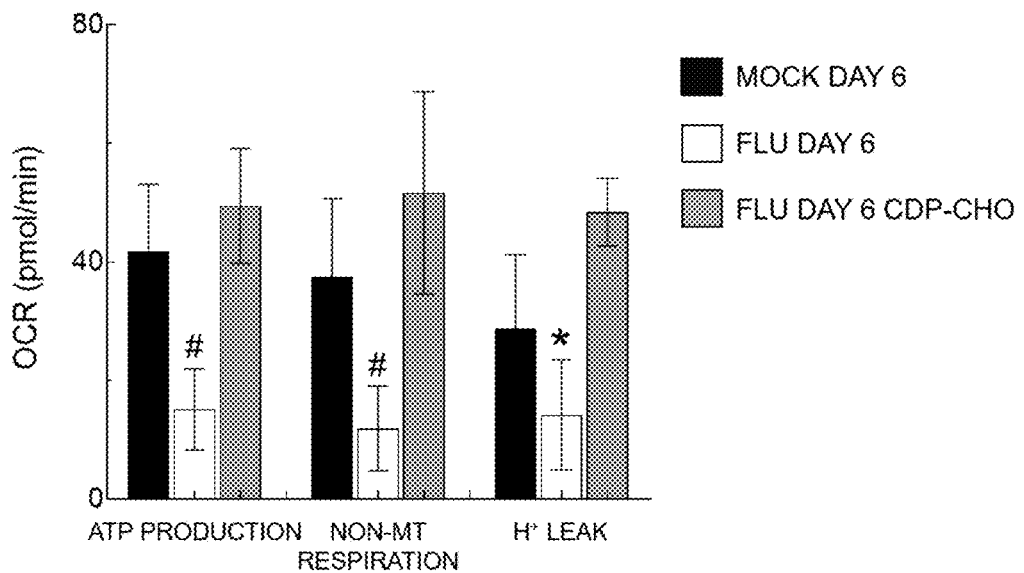
FIG. 18 is a plot showing effect of daily i.p. treatment with CDP-choline (CDP-CHO, 100 μg/mouse) from 1-5 days post-influenza infection on ATP production, non-mitochondrial (non-mt) respiration, and proton ($H^+$) leak of alveolar type II (ATII) epithelial cells isolated at 6 days post-mock infection or 6 days post-influenza infection. $*=P<0.05$, $\#=P<0.001$. These data were generated using the Seahorse MitoStress test kit on a Seahorse XFe24 Analyzer (Agilent, Santa Clara, Calif.) in accordance with manufacturer's instructions. The results demonstrate that influenza infection impairs ATII cell mitochondrial ATP synthesis, non-mitochondrial respiration, and the coupling efficiency between mitochondrial substrate oxidation and ADP phosphorylation (H+ leak) and demonstrate that these mitochondrial effects are reversed by treatment with CDP-choline.

Influenza infection impairs ATII cell mitochondrial ATP synthesis, glycolysis, and the coupling efficiency between mitochondrial substrate oxidation and ADP phosphorylation (H+ leak), and demonstrate that these effects are reversed by treatment with CDP-choline (FIG. 18). To generate these data alveolar type II (ATII) epithelial cells were isolated at 6 days post-mock infection or 6 days post-influenza infection and immediately subjected to analysis using the Seahorse MitoStress Kit on a Seahorse XFe24 Analyzer (both Agilent, Santa Clara, Calif.) in accordance with manufacturer's instructions.

Figure 19:
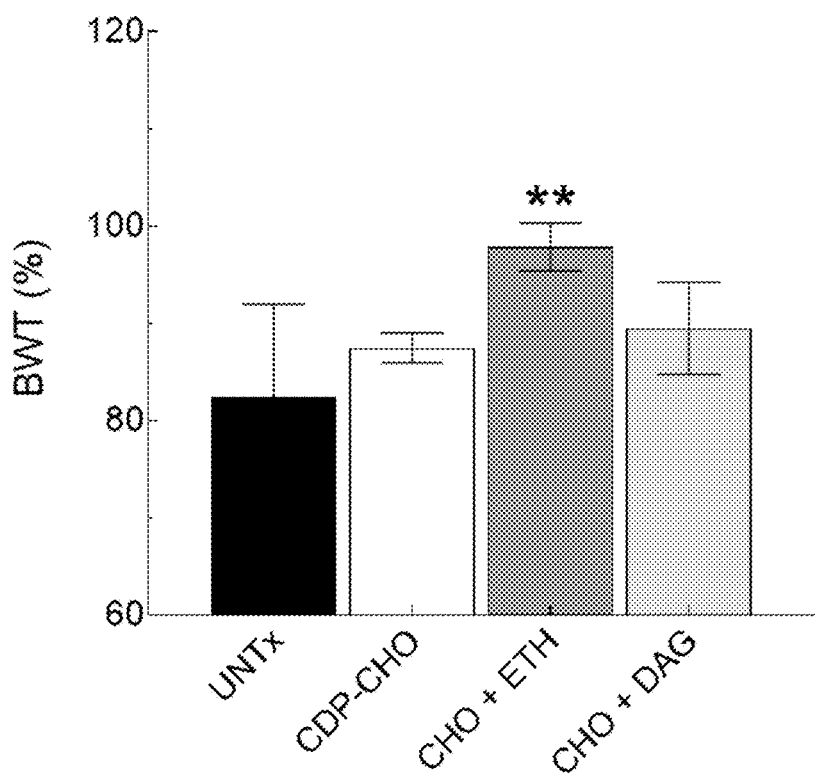
FIG. 19 is a plot showing effect of daily i.p. treatment with CDP-choline (CDP-CHO, 100 μg/mouse), CDP-choline+ 100 μg/mouse CDP-ethanolamine (CHO+ETH), and CDP-choline+10 μg/mouse CDP-diacylglycerol 16:0/16:0 (CHO+DAG) from days 1-6 on mouse weight loss (shown as % of starting body weight [BWT]) at day 7 after intranasal administration of bleomycin (0.1 mg/mouse) to induce ARDS. $**=P<0.005$. These data demonstrate that treatment with CDP-choline+CDP-ethanolamine can attenuate cachexia in mice with ARDS cause by a chemical (non-infectious) insult. In contrast, treatment with CDP-choline alone, or in combination with CDP-DAG has no such beneficial effect. These also are multi-therapeutic component effects.

Treatment with CDP-choline+CDP-ethanolamine can attenuate cachexia in mice with ARDS cause by a chemical (non-infectious) insult (FIG. 19).

Figure 20:
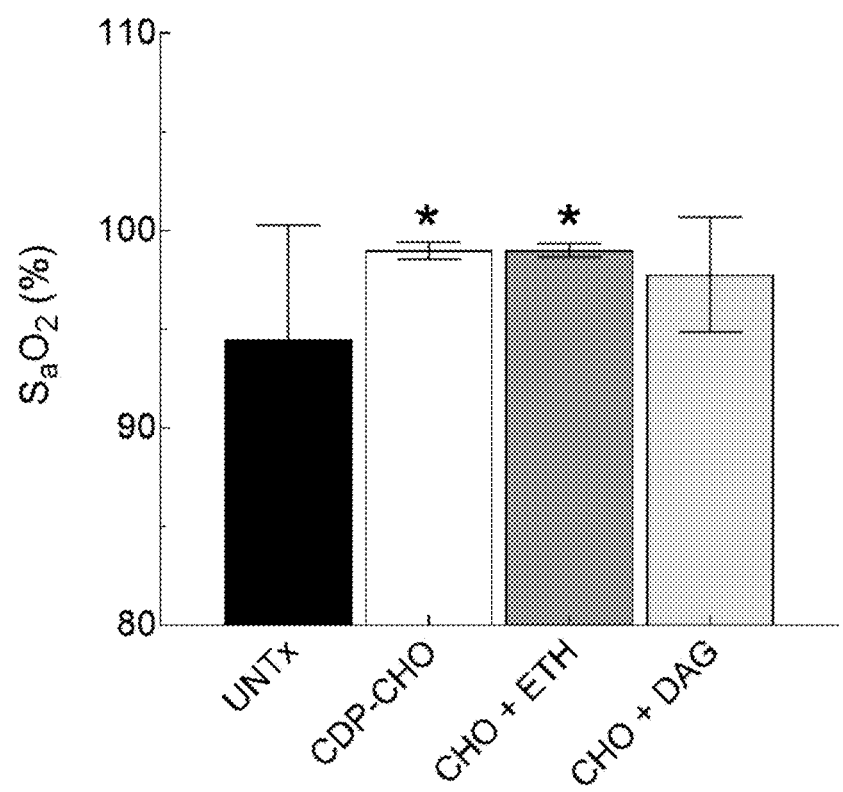
FIG. 20 is a plot showing effect of daily i.p. treatment with CDP-choline (CDP-CHO, 100 μg/mouse), CDP-choline+ 100 μg/mouse CDP-ethanolamine (CHO+ETH), and CDP-choline+10 μg/mouse CDP-diacylglycerol 16:0/16:0 (CHO+DAG) from days 1-6 on mouse O2 sats (SaO2) at day 7 after intranasal administration of bleomycin (0.1 mg/mouse) to induce ARDS. $*=P<0.05$. These data demonstrate that treatment with CDP-choline or CDP-choline+ CDP-ethanolamine can attenuate hypoxemia in mice with ARDS cause by a chemical (non-infectious) insult. These also are multi-therapeutic component effects.

Treatment with CDP-choline or CDP-choline+CDP-ethanolamine can attenuate hypoxemia in mice with ARDS cause by a chemical (non-infectious) insult (FIG. 20).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A composition comprising two or more cytidine diphosphate (CDP)-conjugated precursor in a pharmaceutically acceptable carrier, wherein the CDP-conjugated precursor comprises CDP-diacylglycerol (CDP-DAG) and CDP-choline, CDP-ethanolamine, or a variant thereof having a chemical modification selected from the group consisting of methylation, esterification, amidation, nitration, nitrosylation, oxidation, sulfation, acetylation, alcoholysis, acidolysis, biotinylation, and fluorophore conjugation, wherein CDP-conjugated precursors are the only active ingredient in thee composition.

2. The composition of claim 1, consisting essentially of CDP-choline and CDP-DAG in a pharmaceutically acceptable carrier.

3. The composition of claim 1, comprising CDP-choline, CDP-DAG, and CDP-ethanolamine.

4. The composition of claim 1, wherein the CDP-conjugated precursors are the only active ingredients in the composition.

5. The composition of claim 1, wherein the composition is in a powder or tablet form.

6. A method for treating an acute respiratory distress syndrome (ARDS) in a subject, comprising administering to the subject an effective amount of the composition of claim 1.

7. A method for treating an acute respiratory distress syndrome (ARDS) in a subject, comprising administering to the subject an effective amount of a composition comprising one or more cytidine diphosphate (CDP)-conjugated precursors selected from the group consisting of CDP-choline, CDP-ethanolamine, CDP-diacylglycerol (CDP-DAG), and combinations thereof, wherein CDP-conjugated precursors are the only active ingredient, and wherein the composition is administered after the subject has developed ARDS.

8. The method of claim 7, wherein an effective amount of the composition is at least 0.1 ng per kg of body weight.

9. The method of claim 7, wherein the composition comprises two or more cytidine diphosphate (CDP)-conjugated precursors selected from the group consisting of CDP-choline, CDP-ethanolamine, and CDP-diacylglycerol (CDP-DAG), in a pharmaceutically acceptable carrier.

10. The method of claim 7, wherein the composition is administered intravenously, orally, or by inhalation.

11. The method of claim 7, wherein the ARDS is caused a direct lung insult.

12. The method of claim 11, wherein the direct lung insult is selected from the group consisting of a viral, bacterial, or fungal infection; toxic gas inhalation; a lung cancer; chemotherapy; acid aspiration; and chest trauma.

13. The method of claim 12, wherein the infection comprises influenza.

14. The method of claim 7, wherein the ARDS is caused an indirect result of trauma to other body regions.

15. The method of claim 14, wherein the trauma is selected from the group consisting of sepsis, ischemia/reperfusion, and surgery.

16. The method of claim 6, wherein the composition is administered to the subject prior to infection with one or more influenza virus strains.

17. The method of claim 6, wherein the composition is administered after the subject has been infected with one or more influenza virus strains but before said subject has developed ARDS.

18. The method of claim 8, wherein the composition comprises CDP-diacylglycerol (CDP-DAG).

19. The method of claim 7, wherein the composition is in a powder or tablet form.

20. The method of claim 7, wherein the composition comprises CDP-choline.

21. The method of claim 7, consisting essentially of CDP-choline and CDP-DAG in a pharmaceutically acceptable carrier.

22. The method of claim 7, comprising CDP-choline, CDP-DAG, and CDP-ethanolamine.

23. A method for treating an acute respiratory distress syndrome (ARDS) in a subject, comprising administering to the subject an effective amount of a composition comprising one or more cytidine diphosphate (CDP)-conjugated precursors selected from the group consisting of CDP-choline, CDP-ethanolamine, CDP-diacylglycerol (CDP-DAG), and combinations thereof, wherein the composition does not comprise a nucleotide, and wherein the composition is administered after the subject has developed ARDS.

24. The method of claim 23, wherein the composition is administered intravenously, orally, or by inhalation.

25. The method of claim 23, wherein the ARDS is caused by a direct lung insult.

26. The method of claim 25, wherein the direct lung insult is selected from the group consisting of a viral, bacterial, or fungal infection; toxic gas inhalation; a lung cancer; chemotherapy; acid aspiration; and chest trauma.

27. The method of claim 26, wherein the infection comprises influenza.

28. The method of claim 23, wherein the ARDS is caused an indirect result of trauma to other body regions.

29. The method of claim 28, wherein the trauma is selected from the group consisting of sepsis, ischemia/reperfusion, and surgery.

30. The method of claim 23, wherein the composition is administered to the subject prior to infection with one or more influenza virus strains.

31. The method of claim 23, wherein the composition is administered after the subject has been infected with one or more influenza virus strains but before said subject has developed ARDS.

32. The method of claim 23, wherein the composition is in a powder or tablet form.

33. The method of claim 23, wherein the composition comprises two or more cytidine diphosphate (CDP)-conjugated precursors selected from the group consisting of CDP-choline, CDP-ethanolamine, and CDP-diacylglycerol (CDP-DAG), in a pharmaceutically acceptable carrier.

34. The method of claim 23, wherein the composition comprises CDP-choline.

35. The method of claim 23, consisting essentially of CDP-choline and CDP-DAG in a pharmaceutically acceptable carrier.

36. The method of claim 23, comprising CDP-choline, CDP-DAG, and CDEP-ethanolamine.

\* \* \* \* \*